United States Patent [19]
Stayton

[11] Patent Number: 6,165,750
[45] Date of Patent: Dec. 26, 2000

[54] MODIFIED-AFFINITY STREPTAVIDIN

[75] Inventor: Patrick S. Stayton, Seattle, Wash.

[73] Assignee: University of Washington, Seattle, Wash.

[21] Appl. No.: 09/035,665

[22] Filed: Mar. 5, 1998

Related U.S. Application Data

[63] Continuation of application No. 08/387,055, Feb. 9, 1995.

[51] Int. Cl.$^7$ ............................ C12N 15/09; C12N 15/31; C07K 14/36; C07K 1/22
[52] U.S. Cl. ...................... 435/69.1; 435/471; 435/252.3; 435/320.1; 530/350; 530/413; 536/23.7
[58] Field of Search ........................... 530/350; 435/69.1, 435/252.3, 471, 64.1

[56] References Cited

U.S. PATENT DOCUMENTS

| | | | |
|---|---|---|---|
| 4,839,293 | 6/1989 | Cantor et al. . | |
| 5,135,876 | 8/1992 | Andrade et al. . | |
| 5,168,049 | 12/1992 | Meade et al. . | |
| 5,215,927 | 6/1993 | Berenson et al. . | |
| 5,252,466 | 10/1993 | Cronan, Jr. .............................. | 435/69.7 |
| 5,272,254 | 12/1993 | Meade et al. ........................... | 530/350 |
| 5,489,528 | 2/1996 | Kopetzki et al. ..................... | 435/240.2 |
| 5,672,691 | 9/1997 | Kopetzki et al. ....................... | 530/413 |

FOREIGN PATENT DOCUMENTS

| | | |
|---|---|---|
| 198015 B2 | 7/1995 | European Pat. Off. . |
| 89/03422 | 4/1989 | WIPO . |
| WO 93/09144 | 10/1992 | WIPO . |

OTHER PUBLICATIONS

Bayer, E. A., et al., Analytical Biochemistry, vol. 154, "A sensitive assay for biotin, avidin and streptavidin", pp. 367–370, 1986.

Argarana et al., "Molecule Cloning and Nucleotide Sequence of the Streptavidin Gene," *Nucl. Acids Res.* 14:1871–1882 (1986).

Chilkoti et al., Proceedings of Nat'l. Acad. Sci., USA, vol. 92:1754–1758 (1995).

Erijman and Weber, "Oligomeric Protein Associations: Transition from Stochastic to Deterministic Equilbrium," *Biochemistry* 30: 1595–1599 (1991).

Erijman and Weber, "Use of Sensitized Flourescence for the Study of the Exchange of Subunits in Protein Aggregates," *Photochem. Photobiol.* 57:411–415 (1993).

Gitlin et al., Biochem J. 256:279–282 (1988).

Hendrickson et al., "Crystal Structure of Core Streptavidin Determined From Multiwavelength Anomalous Diffraction of Synchrontron Radiation," *Proc. Natl. Acad. Sci. USA* 86:2190–2194 (1989).

Jin et al., "High Resolution Functional Analysis of Antibody–Antigen Interactions," *J. Mol. Biol.* 226:851–865 (1992).

Kurzban et al., "The Quaternary Structure of Streptavidin in Urea," *J. Biol. Chem.* 266:14470–14477 (1991).

Matthews and van Holde, Biochemistry, Chap. 5., pp. 137–141, Benjamin/Cummings Publish. Co. California (1990).

Meyer et al., "Streptavidin–Biotin Immunotoxins: A New Approach to Purging Bone Marrow," *Exp. Hematol.* 19:710–713 (1991).

(List continued on next page.)

*Primary Examiner*—Ponnathapu Achutamurthy
*Assistant Examiner*—William W. Moore
*Attorney, Agent, or Firm*—Arnall Golden & Gregory, LLP

[57] ABSTRACT

Streptavidin tetramers have at least one monomer containing an amino acid modification that produces a reduced binding affinity for biotin, a modified off-rate, a modified on-rate, or an altered binding enthalpy. Polynucleotides encoding the modified monomers are also provided. The modified streptavidin and chimeric streptavidin molecules are useful in methods of bioseparations and cell sorting, imaging, drug delivery, and diagnostics.

15 Claims, 7 Drawing Sheets

OTHER PUBLICATIONS

Miyamoto et al., "Absolute and Relative Binding Free Energy Calculations of the Interaction of Biotin and Its Analogs with Streptavidin Using Molecular Dynamics/Free Energy Perturbation Approaches," *Proteins* 16:226–245 (1993).

Miyamoto and Kollman, "What Determines the Strength of Noncovalent Association of Ligands to Proteins in Aqueous Solution?" *Proc. Natl. Acad. Sci. USA* 90:8402–8406 (1993).

Sano et al., "Expression of a Cloned Streptavidin Gene in *Escherichia coli*," *Proc. Natl. Acad. Sci. USA* 87:142–146 (1990).

Sano and Cantor, "A Streptavidin–Protein A Chimera That Allows One–Step Production of a Variety of Specific Antibody Conjugates," *Bio/Technology* 9:1378–1381 (1991).

Sano and Cantor, "Expression Vectors for Streptavidin–Containing Chimeric Proteins," *Biochem. Biophys. Res. Commun.* 176:571–577 (1991).

Savage et al., Avidin–Biotin Chemistry: A Handbook, Pierce Chemical Co. (1992).

Schwartz et al., "Observation of Noncovalent Complexes to the Avidin Tetramer by Electrospray Ionization Mass Spectrometry," *J. Amer. Soc. Mass Spectrom.* 5:201–204 (1994).

Sligar et al., "Mutagenesis of Cytochromas P450cam and $b_5$," *Meth. Enzymol.,* 206:31–49 (1990).

Sowdhamini et al., "Stereochemical Modeling of Disulfide Bridges. Criteria for Introduction into Proteins by Site–directed Mutagenesis," *Protein Eng.* 3:95–103 (1989).

Takei et al., "Temperature–Responsive Bioconjugates. 1. Synthesis of Temperature–Responsive Oligomers with Reactive End Groups and Their Coupling to Biomolecules," *Bioconjugate Chem.* 4:42–46 (1993).

Weber et al., "Structural Origins of High–Affinity Biotin Binding to Streptavidin," *Science* 243:85–88 (1989).

Wilchek and Bayer, "Introduction to Avidin–Biotin Technology," *Meths. Enzymol.* 184:5–45 (1990).

Willner et al., "Photoswitchable Binding of Substrates to Proteins: Photoregulated Binding of a α–D–Mannopyranose to Concanavalin A Modified by a Thiophenefulgide Dye," *J. Am. Chem. Soc.* 114:3150–3151 (1992).

Zoller et al., Meth. Enzymol. 100:469–501 (1983).

Chilkoti et al. Bioconjugate J., vol. 5:504–507 (1993).

MODIFIED-AFFINITY STREPTAVIDIN

This application is a continuation of Ser. No. 08/387,055, filed Feb. 9, 1995.

GOVERNMENT SUPPORT

Certain embodiments of the invention described herein were made in the course of work supported by the National Science Foundation. Therefore, the U.S. Government has certain rights in this invention.

BACKGROUND OF THE INVENTION

Streptavidin, a protein produced by *Streptomyces avidinii*, forms a very strong and specific non-covalent complex with the water soluble vitamin biotin. Streptavidin is a tetrameric protein that binds biotin with an affinity that is amongst the highest displayed for non-covalent interactions between a ligand and protein, with an association constant (Ka) estimated to be in the range of $10^{13}M^{-1}$ to $10^{15}M^{-1}$. This binding affinity is strong enough to be essentially irreversible under normal physiological solution conditions, and provides the basis for streptavidin and biotin's usefulness in a wide variety of clinical and industrial applications. See, Green, *Adv. Prot. Chem.* 29: 85–143 (1975).

Both streptavidin and the homologous protein avidin, which shares its high affinity for biotin, have been studied as paradigms of strong ligand-protein interactions. The X-ray crystal structures of streptavidin and avidin, both in their apo and holo forms, have been described. The sequences of both have also been reported, as have the construction of several streptavidin fusion proteins (Sano and Cantor, *Biochem. Biophys. Res. Commun.* 176: 571–577 (1991); U.S. Pat. No. 4,839,293). The structure-function origins of the unusually high affinity, however, have yet to be elucidated.

The streptavidin molecule displays a number of the common recognition motifs that have been identified for protein-ligand binding interactions. These include van der Waals dispersive attractions, which are largely mediated by the aromatic side chains of tryptophan residues, hydrogen bonding networks mediated by donor/acceptor side chains, and disorder-to-order transitions mediated by the ordering of surface polypeptide loops upon ligand binding.

Miyamoto and Kollman have reported a computational study that emphasizes the importance of hydrophobic/van der Waals dispersive attraction between ligand and protein. Miyamoto and Kollman, *Proteins* 16: 226–245 (1993) and *Proc. Natl. Acad. Sci. USA* 90: 8402–8406 (1993). These studies suggest that hydrophobic/van der Waals interactions contribute ~18 kcal/mol to the absolute free energy of binding, while the electrostatic energy term (which includes hydrogen bonding interactions) contributes only ~3 kcal/mol.

In addition to the extremely high binding affinity, the usefulness of streptavidin also arises from the unique architectural properties of the protein. Streptavidin is a tetramer of four identical subunits, with each subunit contributing a binding site for biotin. Because the tetramer has approximate two-fold symmetry, the binding sites are positioned in pairs on opposite sides of the molecule, making the protein an efficient molecular adaptor. This structural feature, along with the high affinity of streptavidin for biotin, has made the protein an important component in many technologies.

While the streptavidin tetramer displays nearly ideal 222 point group symmetry, there are two distinct protein-protein interfaces within the tetramer. Hendrickson et al., *Proc. Natl. Acad. Sci. USA* 86: 2190–2194 (1989); Weber et al., *Science* 243:85–88 (1989). The first interface lies between two monomers that are related by the two-fold symmetry axis, and is defined by an extensive overlap of β-barrel surfaces with complementary curvatures. This interface is characterized by a number of van der Waals, hydrogen bonding, and salt-bridge interactions. The close association of subunits at this interface defines the streptavidin diner, with biotin binding sites related by the two-fold symmetry axis. The second tetramer interface defines the surface between pairs of these closely associated dimers (streptavidin is well described as a "dimer of dimers"). The dimer/dimer interface is characterized by a very loose "waistline" with minimal bonding interactions mediated largely by the C-terminal β-strand 8 of the monomers. Thus, the dimer interface is structurally extensive while the dimer/dimer interface is structurally minimal. Despite the apparent lack of strong bonding interactions at the dimer/dimer interface, the streptavidin tetramer is exceedingly stable in both the biotin-free and biotin-bound states. The tetramer does not dissociate into smaller subunits in either 6 M urea or 6 M guanidinium hydrochloride. Kurzban et al., *J. Biol. Chem.* 266: 14470–14477 (1991). The biotin binding site is defined by a plurality of amino acid residues, as shown, for example, by FIG. 3 of Weber et al.

Streptavidin and avidin are key components in four technological areas of great significance: 1) bioseparations/cell sorting; 2) imaging; 3) drug delivery; and 4) diagnostics (Wilchek and Bayer, in *Meths. Enzymol.* 184: 5–45 (1990)). In the separations area, these proteins have been used extensively in important cell sorting applications, where for example they are used to remove contaminating cells from hematopoietic stem cells prior to marrow transplantation. Berenson et al., *Prog. Clin. Biol. Res.* 377: 449–459 (1992). They have found similar wide use in cancer diagnostics, where they are used extensively in both research and clinical settings to test for the presence of various tumor specific biomarkers.

The imaging and drug delivery applications of streptavidin/avidin and biotin arise from the capability for simultaneous targeting and delivery of imaging agents or therapeutics to tumor cells. There is particularly significant emerging interest in the use of streptavidin/avidin for targeted delivery of imaging agents and therapeutics in vivo. Streptavidin/avidin has been used to deliver drugs, toxins and imaging agents to targeted cells both in vitro and in vivo. See, e.g., Meyer et al., *Exp. Hematol.* 19: 710–713 (1991). In these systems, streptavidin plays the crucial role of molecular adaptor between an antibody that serves as the targeting component, and a biotinylated therapeutic or imaging agent. With some strategies, cells are pre-targeted with the antibody-streptavidin conjugate, with subsequent delivery of the biotinylated agent. In other applications, a biotinylated antibody is first used to pre-target cells, with subsequent delivery of the streptavidin-biotinylated agent conjugate. A three-step delivery is also possible, using biotinylated antibody followed by streptavidin and then the biotinylated agent.

While streptavidin and avidin are incredibly useful molecules, they have important limitations, such as the inflexibility of four identical subunits having binding sites with extremely high affinity. Further, it has not been feasible to control the distribution of the subunits within the tetramer if the degeneracy of the subunits is removed (e.g., subunits with different affinities, subunits labeled with different imaging agents, subunits labeled with different drugs).

What is needed in the art is the ability to tailor the functional properties of individual subunits, and their geometrical distribution within the tetramer. This can be accomplished by manipulating important streptavidin structure-function relationships. A library of streptavidin mutants spanning a range of affinities and off- and on-rates for biotin and its derivatives would improve upon existing biotechnological applications for this already widely used system and open it to important new uses. Similarly, the ability to precisely define the subunit components and geometry will dramatically improve existing applications and provide new tools for cell separations, imaging, therapeutics and a variety of other technologies. Quite surprisingly, the present invention fulfills these and other related needs.

SUMMARY OF THE INVENTION

The present invention provides a streptavidin tetramer where at least one monomer of the tetramer has an amino acid modification that produces a reduced binding affinity for biotin, a modified off-rate, a modified on-rate, and/or an altered binding enthalpy. The resulting binding affinity of the tetramer for biotin is less than approximately $1 \times 10^{13}$ $M^{-1}$. Typically, at least one monomer of the streptavidin tetramer will have an amino acid modification that results in the reduced binding affinity for biotin, sometimes at least two or three monomers, and in some embodiments all four monomers which comprise the tetramer have an amino acid modification that results in the reduced binding affinity for biotin. In a preferred embodiment, the amino acid modification is a substitution of a tryptophan residue in a biotin binding site, such as the tryptophan residue at amino acid position 79, 92, 108 or 120. The tryptophan residue of at least two of the foregoing amino acid positions can be substituted or deleted. Conveniently, any of the amino acids other than tryptophan lowers the binding affinity and results in a faster off-rate; phenylalanine or alanine are preferred substitutions for the tryptophan residue in the biotin binding site described in the illustrative examples described herein.

The invention also provides an isolated polynucleotide molecule which encodes streptavidin having an amino acid modification that results in a reduced binding affinity of streptavidin for biotin. In representative embodiments the polynucleotide molecule encodes an amino acid substitution or deletion of a tryptophan residue in a biotin binding site, such as a tryptophan residue at amino acid position 79, 92, 108 or 120, e.g., by substituting a phenylalanine or alanine residue or other amino acid residue. The isolated polynucleotide molecule may encode substitutions of at least one of said amino acid positions, sometimes two or more.

In other aspects the invention provides a method for producing a streptavidin tetramer with at least one monomer thereof having a characteristic not found in a native streptavidin monomer subunit which characteristic affects affinity but not specificity for biotin. The method comprises producing altered streptavidin tetramer having the characteristic, separating the altered streptavidin into monomer and/or diner subunits, e.g., by guanidium thiocyanate refolding; and mixing the streptavidin monomer and/or dimer subunits with streptavidin monomer or diner subunits which do not have the characteristic, thereby producing a streptavidin tetramer having at least one monomer thereof with said characteristic. The method can also be used to assemble chimeric tetramers where at least one of the monomers but less than all contains a label, drug, toxin, targeting molecule, metal, or an amino acid modification that results in a reduced binding affinity of streptavidin for biotin. For example, the streptavidin monomer may contain at least one mutation in the amino acid sequence thereof which is situated at the dimer/dimer interface, e.g., a disulfide bond can be engineered to connect specific subunits and define the stoichiometry of the dissociated species.

BRIEF DESCRIPTION OF THE DRAWINGS

FIG. 4A is WT streptavidin (filled circle), W79F (open triangle), and W108F (open square); and FIG. 4B is W120F (open circle).

FIG. 6A is 2-iminobiotin affinity chromatography; protein was bound to iminobiotin column equilibrated in pH 11 binding buffer, washed with binding buffer, and eluted with pH 4 buffer; FIG. 6B is biotin affinity chromatography: bound protein from FIG. 6A was incubated with biotin, and exhaustively ultrafiltered to specifically block with WT subunits with biotin and passed over biotin column; protein was bound to the biotin column in PBS and eluted with 2 mM biotin in PBS.

DESCRIPTION OF THE SPECIFIC EMBODIMENTS

Figure 1:
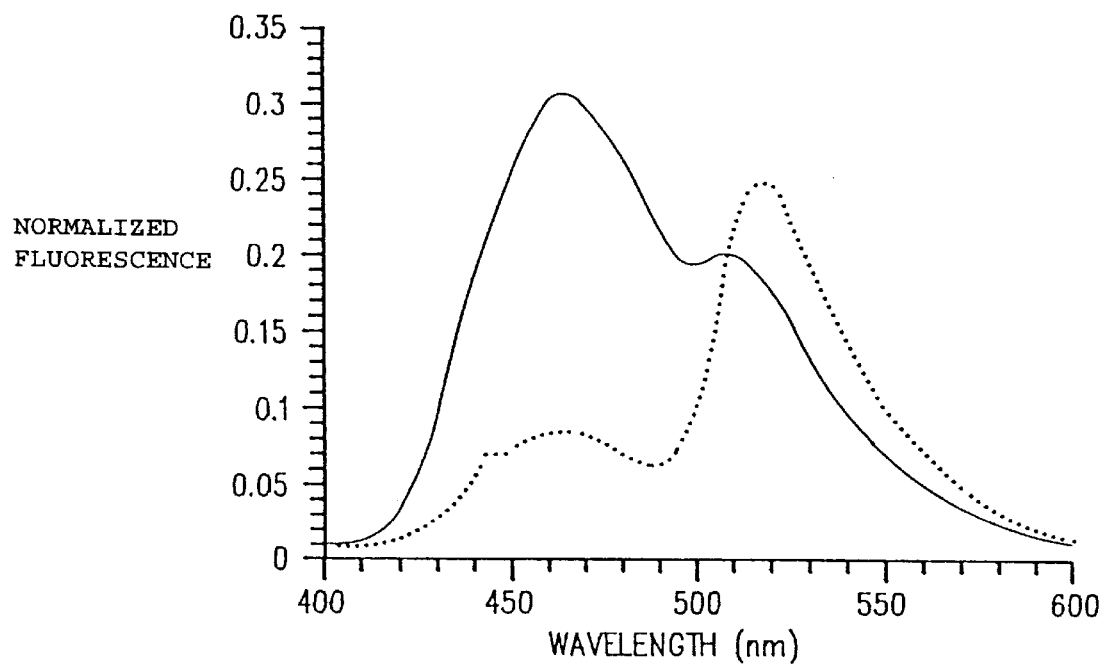
FIG. 1 demonstrates mixing of subunits with different labels to form chimeric tetramers by using the fluorescence resonance energy transfer of CPI-and FITC-labeled WT streptavidin after guanidine thiocyanate induced dissociation. The solid line is the emission spectrum (ex=385 nm) after mixing the CPI-and FITC labeled WT streptavidin tetramers at pH 8.6. The dotted line shows a decrease in the donor emission spectrum (CPI) with a corresponding increase in the emission spectrum of the fluorescence energy acceptor (FITC). The emission spectrum of similarly mixed CPI-and FITC-labeled WT streptavidin which had not undergone denaturation/renaturation, is the sum of the individual spectrum of the two components. The tryptophan emission intensity and spectral center of mass were recovered after guanidine unfolding. The fluorescence spectra are normalized to the integrated intensity of their tryptophan emission, to correct for dilution effects arising from dialysis of the mixed tetramer.

The present invention provides streptavidin and avidin molecular adaptors which are chimeric in that the streptavidin tetramers have heterologous, but defined, subunit composition and function. In other aspects of the invention the position of the heterologous subunits within the streptavidin tetramer can be controlled. Chimeric streptavidin tetramers are provided by employing genetic engineering techniques and biophysical tetramer dissociation/reassembly procedures. The chimeric streptavidin and avidin molecular adaptors provide a wide variety of uses, including new approaches to therapeutic-related drug delivery, the in vivo delivery of imaging agents, cell sorting and separations, and diagnostic applications.

The chimeric streptavidin tetramers are produced by a controlled mixing of subunits, where one or more of the subunits have properties that are desired for a particular utility. For example, a subunit with a decreased affinity for biotin when compared to wild-type streptavidin will be able to release an anti-neoplastic agent to which it is conjugated more easily than if conjugated to the wild-type streptavidin subunit. Of course, the individual subunits or dimers thereof can have properties other than, or in addition to, an altered binding affinity for biotin.

The production of the streptavidin subunit having the altered characteristics can be accomplished by several routes depending on the intended use and the characteristic of the subunit which is modified. For example, in some instances subunits, dissociated or nondissociated, may be labeled, directly or indirectly, with a fluorescent or radionuclide label or the like, or linked to another compound, etc., and then dissociated (if not already dissociated) and mixed with other subunits as described herein to form the chimeric tetramers.

In certain embodiments described herein the streptavidin subunits have a reduced binding affinity for biotin (or iminobiotin), e.g., by means of amino acid substitutions or deletions in residues of the biotin binding domain, and especially by changing the Trp residues at positions 79, 92, 108 and/or 120. Such characteristic resulting in the reduced binding affinity are accomplished by recombinant DNA techniques, where the specific amino acid residues of the streptavidin polypeptide are altered, e.g., by site-directed mutagenesis. Although examples of mutations which result in diminished affinity of the streptavidin polypeptide for biotin are described in the Example section below, where alterations at Trp79, Trp92, Trp108 and Trp120 result in a diminished binding, additional alterations based on the teachings hereof may be employed. For example, any of the amino acids other than Trp may be substituted at the selected position(s). The reduced binding affinities of the altered streptavidin for biotin (and/or iminobiotin) will typically be less than approximately $1 \times 10^{13}$ M$^{-1}$, sometimes less than about $1 \times 10^{12}$ M$^{-1}$, sometimes less than or equal to about $1 \times 10^{11}$ M$^{-1}$, and in some cases as low as about $1 \times 10^{10}$ M$^{-1}$ or lower, e.g., $1 \times 10^{7}$ M$^{-1}$.

In addition to engineering changes in streptavidin's biotin binding site for biotin to reduce the binding affinity, on-rate or off-rate, other mutations to subunits or dimers of streptavidin can be made. These include, for example, engineering of enhanced dissociation equilibria to destabilize the dimer/dimer interface through site-directed mutagenesis of side-chains at the dimer/dimer interface. For example, the streptavidin monomer may contain at least one mutation in the amino acid residues situated at the dimer/dimer interface. In this case a disulfide bond can be engineered to connect specific subunits and define the stoichiometry of the dissociated species. Alternatively, an enhanced sensitivity to hydrostatic pressure can be engineered, without altering solution stability, at the dimer/dimer interface. Other mutations can be made to the subunits to permit attachment of drugs, linkers, enzymes, labels, etc.

Once the streptavidin subunits have been modified to possess the desired characteristic, different subunits, e.g., modified and wildtype, are mixed to reform a heterologous or chimeric streptavidin tetramer having one, two or three modified subunits. Homologous tetramers having modified subunits in each position are formed by refolding the modified subunits and do not require mixing. The subunits can be cross-linked to form diners and the same or different dimers reassociated to form the heterologous tetramer, or the subunits can be simply mixed at the monomer level to form 1:3, 2:2 and 3:1 modified tetramers. Thus, a wide variety of combinations are made possible by the present invention.

Subunit mixing within the streptavidin tetramer can be monitored by a variety of different techniques. In one technique, a fluorescence assay is used to follow the mixing of oligomeric protein subunits after dissociation by high pressure, as generally described in Erijman and Weber, *Biochemistry* 30: 1595–1599 (1991), incorporated by reference herein. In this assay, one population of the oligomeric protein is labeled with a fluorescence energy transfer donor, e.g., 7-diethylamino-3-(4'-isothiocyanatophenyl)-4-methylcoumarin, and a second population is labeled with a complementary energy transfer acceptor, e.g., fluorescein isothiocyanate. Sulfhydryl-selective derivatives of these fluorophores can be used to label a site-directed mutant which has been constructed to provide a stoichiometric labeling site for thiol-specific small molecules, e.g., the Asn49Cys mutant, which will provide one fluorophore donor or acceptor per subunit. When the two populations are mixed at ambient conditions, the fluorescence emission spectrum is simply the addition of the individual donor and acceptor spectra. This is because the dissociation rates of oligomeric proteins are generally negligible and so there is no mixing of the two populations. When the mixed proteins are exposed to denaturants where the dissociated states are populated, and then brought back to ambient conditions, the fluorescence emission is altered by energy transfer. The excitation wavelength for energy transfer studies with this donor/acceptor pair is 385 nm and the emission spectra are collected from 400 nm to 600 nm. This energy transfer spectrum is diagnostic of mixing between the donor-labeled subunits with acceptor-labeled subunits, where some of the reassociated oligomers have the donor and acceptor labels present on the same molecule.

Thus, the monitoring technique can be used to demonstrate subunit mixing after denaturant-induced tetramer dissociation. In one example, a recombinant streptavidin population was labeled with the coumarin fluorophore, and a second population with a fluorescein derivative. These populations were mixed and the fluorescence emission spectrum shown by the solid line in FIG. 1 was obtained. The sample was then brought to 6 M guanidinium thiocyanate for 1 hr and then dialyzed back to the starting conditions. The refolding was nearly quantitative as evidenced by the return of the tryptophan fluorescence intensity and emission maximum to those measured under the starting conditions. The dye emission spectra were altered in a manner consistent with the emergence of energy transfer between the coumarin and fluorescein dyes (dotted line, FIG. 1). This experiment provides evidence for subunit mixing after dissociation of the tetramer.

Monitoring the chimeric tetramers of the protein population can also be performed by electrospray mass spectrometry (ESMS). Recent developments in ESMS have allowed the noncovalent association in multisubunit proteins to be preserved, allowing for the detection of the entire, multisubunit complex. See Light-Wahl et al., *J. Amer. Chem. Soc.* 115:5869 (1993); Light Wahl et al., *J. Amer. Chem. Soc.* 116:5271 (1994); and Schwartz et al., *J. Amer. Soc. Mass Spectrom.* 5:201–204 (1994) each of which is incorporated herein by reference. The chimeric streptavidin tetramers are analyzed by ESMS under conditions that favor preservation of noncovalent association. Corroboration of tetramer composition can be obtained by analyzing the protein under conditions that favor dissociation of the tetramer into monomers.

Selective pressure dissociation can also be used for the streptavidin tetramer, particularly where the dimer/dimer interface has been genetically engineered to be susceptible to such dissociation. High pressure techniques are used to dissociate the tetramer into subunits under equilibrium conditions that permit efficient mixing of heterologous subunit populations. Pressure dissociation is generally very gentle and reversible because the physical driving force for pressure induced dissociation is the difference in volume between the tetramer and the isolated subunits. The application of pressure favors the side of the equilibrium with lowest net volume, and in most cases the individual subunits (monomers or dimers) will have a lower net volume than the oligomeric state (tetramer). Thus, application of hydrostatic pressure will generally shift the association equilibrium toward the dissociated states. Thus, dissociation and subunit mixing can be controlled without significantly altering the tetramer stability under ambient conditions. In addition, by introducing charge pairs at specific interfaces via site-directed mutagenesis, pressure-induced dissociation to either the monomer or to the dimer state can be effectuated. This is shown with the dimer-dimer interface, which is minimal and structurally well defined, and can be applied to engineer the pressure sensitivity of the monomer-monomer interface. By engineering the two interfaces (dimer-dimer and monomer-monomer) to have distinct pressure sensitivities, this approach provides means for controlling the species (monomer or dimer) available for mixing—and thus control the architecture of the chimeric binding sites within mixed tetramers. The pressures necessary to mix tetramer subunits are determined using the fluorescence energy transfer and mass spectrometry approaches. Pressure ranges are established that dissociate the tetramer into dimers but not monomers, and that dissociate the tetramer into monomers.

In another aspect, tetramer subunit connectivity is altered by site-directed mutagenesis to introduce residues capable of forming disulfide bonds, and thus control tetramer reassembly via the disulfide bonds. For example, spatially proximal β-carbon positions of the streptavidin protein-protein interfaces are determined where the distance and dihedral geometry is appropriate for engineering disulfide bonds, e.g., positions across the monomer/monomer interface and dimer/dimer interface. A covalent bond is preferably engineered between the monomers in the dimer, for example, at position H127. It is then demonstrated that when dissociation to dimers occurs, a labeled tetramer arising from the tagged disulfide bonded dimer returns.

The mixed streptavidin tetramers with defined subunit composition which are constructed according to the present invention find use in a wide variety of drug delivery and imaging, cell sorting and separation technologies. Streptavidin is used in a number of crucial separations/cell-sorting technologies. The ability to reconstruct mixed streptavidin tetramers with defined subunit orientation as provided by the present invention greatly improves these molecular tools. For example, two subunits can be labeled with fluorescent dye markers without disturbing the affinity of the remaining two sites, thereby ensuring that the label is on one side of the tetramer away from the other two binding sites, and thus not sterically interfering with binding affinity. The site-directed mutants of the invention provide labeling sites for markers or probes, e.g., luminescent agents, radiolabels, enzymes, chromophores, ferritin, hemocyanin, macromolecular carriers, etc., and these can similarly be mixed with wild-type subunits to form chimeric tetramers. The site-directed mutants can also be used to provide sites for immobilizing streptavidin to surfaces such as magnetic beads or chromatography supports and these can be mixed with wild-type subunits to yield sterically optimized cell separations components. Further, the site-directed mutants designed for ordering streptavidin at surfaces can be combined with site-directed mutants that lower the binding affinity, thereby providing components that are sterically optimized and which have affinity that permits more gentle elution of bound cells. Thus, the applications of the modified molecules of the instant invention include, for example, affinity chromatography, affinity cytochemistry, histochemistry, diagnostics, signal amplification, blotting technology, bio-affinity sensors, gene probes, drug delivery, crosslinking agents, affinity targeting, affinity perturbation, fusogenic agent, immobilizing agent, selective retrieval, and selective elimination, among others.

For example, methods for immunoselection of cells using avidin and biotin, in which the lower affinity mutants of the present invention are particularly useful, are described in detail in Berenson et al., U.S. Pat. No. 5,215,927, incorporated herein by reference. In one method for separating a target substance such as a hematopoietic stem cell from a heterogeneous suspension containing the target substance, a suspension such as a cell culture, bone marrow, peripheral blood or cord blood is reacted with a biotinylated binding component which binds to the target substance, thereby forming a biotinylated targeted substance complex. The biotinylated binding component can be an antibody, polyclonal, monoclonal or binding fragment thereof, that binds specifically to CD34+ hematopoietic stem cells. The suspension containing the biotinylated target substance complex is exposed to a modified streptavidin molecule of the present invention, e.g., a chimeric tetramer comprising at least one modified monomer but less than four modified monomers. For convenience, the exposing step can be performed in a column in which the streptavidin tetramer of the invention has been adsorbed to a solid phase. The biotinylated target substance complex is separated from the suspension by means of the lower affinity (or increase in dissociation rate constant) of the modified streptavidin monomer units to recover the target substance in enriched form.

For drug delivery, imaging, and other such uses, a chimeric streptavidin tetramer comprising, e.g., two higher affinity and two lower affinity modified monomers, is loaded with a biotinylated molecule (e.g., biotinylated antibody) such that the biotinylated molecule is selectively partitioned to the higher affinity subunits by virtue of the fast off-rate of the lower affinity subunits. The biotinylated target/chimera complex is targeted to the desired site, either in vivo or ex vivo, via the antibody. A biotinylated imaging agent or drug is administered and captured by the lower affinity subunits, whereby the targeted cells or tissues are thus exposed to the drug or label for the desired site-specific therapeutic or diagnostic activity. In another aspect, a biotinylated targeting agent is administered, followed by a streptavidin chimera of the present invention having high and lower affinity binding sites. The high affinity sites bind to the biotin at the target site. A biotinylated imaging or therapeutic agent is then administered, which binds at the available lower affinity streptavidin sites. This results in a real time release from the streptavidin molecule of the therapeutic or imaging agent at the targeted site. In yet another embodiment, the chimeric streptavidin tetramer of, e.g., two higher affinity and two lower affinity modified monomers, is loaded with a biotinylated molecule such as an antibody (or receptor, ligand etc.) at the higher affinity subunits, and the lower affinity sites are loaded with biotinylated drug, therapeutic protein or imaging label. The chimeric complex is targeted to the desired site or cells in vivo or ex vivo via the targeting component, where the lower affinity component is released to impart the desired therapeutic or diagnostic activity. In yet another example, the lower affinity subunits conjugated to enzymes (e.g., alkaline phosphatase) that are suitable for conversion of prodrugs (e.g., etoposide phosphate) can be mixed with higher affinity subunits conjugated to antibodies or other targeting components, such that when administered to the patient or cell collection the antibody delivers the chimeric complex to the desired site(s) and the enzyme activates prodrug which is administered to the patient or cells. Suitable prodrugs, enzymes, and methods of administration are described in Senter et al., U.S. Pat. No. 4,975,278, incorporated herein by reference.

The following examples are offered by way of illustration, not by way of limitation.

EXAMPLE 1

This Example describes the construction of streptavidin having amino acid modifications of the biotin binding site, which modifications are shown to result in a reduced binding affinity for iminobiotin and biotin.

Design and Construction of a Synthetic Gene for Core Streptavidin

The program GCG (Genetics Systems Group Inc., Madison, Wis., 1991) was used to generate a nucleotide sequence from the amino acid sequence of core streptavidin, defined as residues 13–139 of the naturally occurring protein (for the sequence of streptavidin see Argarana et al., *Nucl. Acids Res.* 14: 1871–1882 (1986), and U.S. Pat. No. 4,839,293, each of which is incorporated herein by reference). The synthetic gene for core streptavidin incorporates favorable *E. coli* codon usage (deBoer et al., *Maximizing Gene Expression,* eds., Reznikoff et al. (Butterworth, Stoneham, Mass., USA) pp. 225–285 (1986)), a consensus ribosome binding site (Shine et al., *Nature* 254: 34–38 (1975)), an initiating methionine codon, translational stop codons, and a number of unique restriction endonuclease recognition sites spaced evenly throughout the length of the gene. These features were incorporated into the gene design to facilitate convenient generation of site-directed mutants by cassette mutagenesis as well as expression from plasmids lacking their own ribosome binding site.

Single stranded oligodeoxyribonucleotides were synthesized commercially (Oligos Etc.) and purified by gel filtration. The core streptavidin gene was constructed in three segments, which were flanked by the following restriction endonuclease recognition sites: EcoRI/XbaI, XbaI/HincII, and HincII/HindIII, respectively. For each segment, individual oligodeoxyribonucleotides were 5'-phosphorylated, annealed, and ligated into a separate PUC18 plasmid that had been linearized with the appropriate pair of restriction endonucleases. (Note that except where explicitly stated otherwise, protocols for standard procedures such as plasmid isolations, ligations, transformations, and digestion with restriction endonucleases are according to Sambrook et al. (Molecular Cloning: A Laboratory Manual, Cold Spring Harbor Laboratory, NY, 2nd Ed. (1989)) or from instructions provided by commercial suppliers of reagents and kits.) The plasmids were subsequently transformed into DH5a, or Novablue (Novagen Inc., Madison, Wis.) *E. coli* cells. Following selection of clones containing the appropriately sized inserts by colony PCR, plasmid constructs were sequenced using dye terminator chemistry with fluorescent detection of sequencing products (Applied Biosystems, Foster City, Calif.). The three DNA segments comprising the core streptavidin gene were isolated and ligated into a single pUC18 plasmid, which was transformed into Novablue cells. At this point, the entire gene was sequenced to confirm the nucleotide sequence. The core streptavidin gene was then subcloned into the *E. coli* expression vector, pET-21a (Novagen Inc.), as an NdeI/HindIII segment and maintained in Novablue cells.

Site-Directed Mutagenesis of Core Streptavidin

W79A, W79F, W108A, and W108F site-directed mutants of WT streptavidin were created by PCR mutagenesis, using mutagenic primers incorporating the desired codon change (Sligar et al., *Meth. Enzymol.,* 206: 31–49 (1990)). The PCR mutagenesis primers were as follows:

W79A (SEQ ID NO:1): 5' TTT CGC AGC AAC GGT CCA ACC CAG AGC GGT TCC AGA A 3';

W79F (SEQ ID NO:2): 5' TTT GAA AGC AAC GGT CCA ACC CAG AGC GGT TCC AGA 3';

W92A (SEQ ID NO:3): 5' ACC GCG TCT GGT CAG TAC GTT GGT GGT GCT GAA 3';

W92F (SEQ ID NO:4): 5' CC TTC TCT GGT CAG TAC GTT GGT GGT GCT G 3';

W108A/F (SEQ ID NO:5): 5' GGT CGT ACC GGA GGT CAG CAG CGA CTG G 3' and (SEQ ID NO:6): 5' GGT CGT ACC GGA GGT CAG CAG GAC CTG G 3';

W108F (SEQ ID NO:7): 5' AG TTC TTG TTG ACC TCC GGC ACC ACC GAA GCT AAC GCT TGG 3'.

W120A and W120F were created by cassette mutagenesis, using the following sequences:

```
Sense Strand 5' -> 3' (SEQ ID NO:8 and SEQ ID NO:9):
CGC GGC TAA ATC CAC CCT GGT TGG TCA CGA CAC CTT CAC CAA AGT
    TT
TAA; and
Antisense strand 5' -> 3' (SEQ ID NO:10 and SEQ ID NO:11):
AG CTT TTA TTA GGA AGC TGC AGA CGG TTT AAC TTT GGT GAA GGT GTC
GTG ACC AAC CAg GGT GGA TTT AGC
                              AA
```

Oligodeoxyribonucleotides, chemically 5'-phosphorylated during synthesis (IDT Inc.), spanning the MluI/HindIII endonuclease restriction sites with degenerate codons at residue 120 incorporating the Trp->Ala/Phe mutation, were annealed, ligated into MluI/HindIII linearized pUC18 containing the core streptavidin gene, and transformed into competent Novablue cells. Clones containing mutant plasmid were identified by the insertion of a PstI restriction site upon successful ligation of the mutagenic insert into the core streptavidin gene. DNA sequencing of plasmids containing a PstI restriction site was used to identify clones containing either the Phe or Ala mutation. The mutant streptavidin genes (W120A or W120F) were subcloned into pET21a as an NdeI/HindIII segment, and maintained in Novablue cells.

Expression of Streptavidin and Mutants in E. coli

The expression plasmid pET-21a containing the streptavidin gene, transformed into the expression host, BL21 (DE3) (Novagen, Inc.), was cultured overnight at 37° C. with shaking, in 10 ml LB medium supplemented with 100 µg/ml ampicillin. The culture was then centrifuged at 4500×g for 5 min, the cell pellet resuspended in fresh 10 ml LB medium and used to inoculate 6.5 L of 2×YT medium supplemented with 100 µg/ml ampicillin in shaker flasks. The culture was incubated with shaking at 37° C. until the absorbance at 600 nm reached 1.0, at which point isopropyl β-D-thiogalactopyranoside was added (1 mM) to induce protein expression. Cells were cultured for a further 3 hrs, after which they were harvested by centrifugation at 4500×g for 10 min. The cell pellets were stored at −70° C. until further use. Quantitation of protein bands in SDS-polyacrylamide gel electrophoresis (PAGE) of induced BL21(DE3) cell lysates by laser densitometry revealed that streptavidin constituted 15–20% of the total cellular protein.

Isolation and Purification of Expressed Streptavidin and Mutants

The frozen cell pellet was thawed, resuspended in 200 ml 50 mM Tris HCl, pH 8.0/0.75 M sucrose/1 mM phenylmethylsulfonyl fluoride (PMSF), and ruptured by sonication. The lysed cells were incubated at room temperature for 15 min with DNAseI (10 µg/ml)/RNAseA (10 µg/ml)/MgCl$_2$ (10 mM), and centrifuged at 22000×g for 30 min. The insoluble fraction was repeatedly washed with 50 mM Tris, pH 8.0/10 mM EDTA/1.5 M NaCl/1 mM PMSF/0.5% (v/v) Triton-X-100 to solubilize membrane proteins. The final white pellet, largely comprising streptavidin inclusion bodies, was approximately 70% pure, as determined by SDS-PAGE. The inclusion bodies were dissolved in 6M guanidine HCl (500 ml), pH 1.5, to a concentration $\leq 50\,\mu$M (streptavidin monomer) and dialyzed against 20 liters 50 mM Tris HCl, pH 8.0/150 mM NaCl/10 mM EDTA/0.1 mM PMSF/0.5 mM benzamidine HCl over 24 h with one 20 L change of dialysis buffer. The dialysate was centrifuged, vacuum filtered through 0.45 µM filters, and concentrated in a stirred ultrafiltration cell (Amicon Inc., Danvers, Mass.). Final concentration to a few ml utilized Centriprep-30 centrifugal concentrators (Amicon Inc.). Insoluble, aggregated protein left over after dialysis can be refolded several times by following the above protocol.

WT Streptavidin and the Trp->Phe mutants were purified by affinity chromatography using iminobiotin-agarose (Pierce, Naperville, Ill.) (46,47). The yield of affinity-purified WT streptavidin was ~10–20 mg per liter of 2×YT culture. The lowered affinity of the Trp->Ala mutants for iminobiotin precluded its use for purification. Instead, the samples were applied to a DEAE-SepharoseFF column (1.5×5 cm) equilibrated with 20 mM Tris HCl, pH 7.0 (Pharmacia, Piscataway, N.J.). Under these conditions, streptavidin does not bind to the column and is eluted in the void volume, though reasonable purification is afforded due to the binding of DNA and most of the contaminant proteins from E. coli. The streptavidin-containing fractions were pooled, concentrated and equilibrated in 20 mM Tris, pH 8.5 and passed over a DEAE-SepharoseFF column (1.5×5 cm) equilibrated in the same buffer. Streptavidin bound under these conditions and was then eluted by applying a linear 0–0.3 M NaCl gradient. Streptavidin-containing fractions were pooled, concentrated and stored at 4° C. for further use. These two chromatography steps afforded homogeneous protein, as verified by SDS-PAGE.

Refolded, affinity-purified WT streptavidin was characterized by amino-acid compositional analysis and N-terminal sequencing. The experimentally-determined composition and the N-terminal sequence, respectively, of the recombinant protein agreed with the calculated composition and sequence of core streptavidin. SDS-PAGE of heat denatured protein showed that the monomers for each Trp mutant were the same size as WT streptavidin monomers, and that the purification methods employed for WT streptavidin and the Trp mutants yielded homogeneous protein, with contaminant proteins below the detection limits of Coomassie staining. ESMS of WT streptavidin and Trp mutants revealed that the experimentally-determined mass of WT streptavidin and Trp mutants were correct. The similar rates of migration of WT streptavidin and Trp mutants in native-PAGE indicated that the refolded mutants self-assembled to form tetramers in solution, similar to WT streptavidin. The binding of fluorescein-biotin to WT streptavidin and the Trp mutants ranged from 0.85 to 1.1 (on a subunit basis) upon saturation, close to the stoichiometric ratio of 1.0 predicted for binding of one biotin per streptavidin subunit.

Characterization of Streptavidin and Mutants

SDS-PAGE analysis was carried out using precast Miniprotean 10–20% gradient gels (BioRad Inc., Richmond, Calif.) with a discontinuous buffer system (Laemmli, Nature 227: 680–685 (1971)). Samples were boiled for 15 min in the presence of SDS before electrophoresis to dissociate streptavidin tetramers. Native-PAGE was performed using the above system by omitting SDS in the sample application buffer and the gel running buffer, as well as the heat denaturation of proteins before electrophoresis. The gels were stained with 0.25% (w/v) Coomassie R-250, dissolved in 45% methanol (v/v), 10% acetic acid (v/v). The concentration of WT streptavidin was determined by absorbance at 280 nm using an extinction coefficient ($e_{280}$) of 34000 M$^{-1}$ cm$^{-1}$ for the subunit (Sano et al., Proc. Natl. Acad. Sci. USA 87: 142–146 (1990)).

Concentrations of the mutants were determined by the method of Gill et al., Anal. Biochem. 182: 319–326 (1989), using $e_{280}$ of WT streptavidin as reference. Protein electrospray mass spectrometry (ESMS) was carried out on an API III electrospray mass spectrometer (PE/Sciex, Thornhill, Ontario). The biotin-binding stoichiometry of WT streptavidin and mutants was determined in solution by the quantitative quenching in the fluorescence of 5-((N-(5-(N-(6-(biotinyl)amino)hexanoyl) amino)pentyl) thioureidyl) fluorescein (Fluorescein-biotin, Molecular Probes, Eugene, OR) upon titration with protein.

ELISA Assays

A modified version of the enzyme assay reported by Bayer et al., Anal. Biochem. 154: 367–370 (1986), was used to examine the concentration-dependent binding of WT streptavidin and mutants with biotin and 2-iminobiotin.

2-Iminobiotin conjugated to bovine serum albumin (iminobiotin/BSA) was synthesized by reacting a twentyfold molar excess of 2-iminobiotin N-hydroxysuccinimide ester (Sigma) with 100 mg BSA in 100 mM NaHCO$_3$, pH 8.3 for 12 hr at 4° C. with end-over-end stirring, followed by dialysis and gel filtration (G-25, Pharmacia) to separate iminobiotin/BSA from unreacted 2-iminobiotin. Biotin/BSA (Pierce) or iminobiotin/BSA at a concentration of 10 mg/ml were adsorbed overnight at 4° C. in 15 mM Na$_2$CO$_3$, pH 9.6, in microwell plates (100 μl per well). The next day the microwell plates were incubated with 200 μl per well of blocking buffer at pH 8.0 or pH 10.0 (50 mM sodium phosphate, pH 8.0 or 50 mM Na$_2$CO$_3$, pH 10.0/100 mM NaCl/0.5% (w/v) BSA/0.05% (v/v) Tween-20) for at least 2 hr at room temperature and then incubated in ten-fold serial dilutions of 100 μg/ml WT streptavidin or mutants (100 μl/well) for 2 hr at room temperature, rinsed with blocking buffer at pH 8.0 or pH 10.0 (200 μl/well), and incubated for 1 hr at room temperature in 2×10$^4$ dilution of primary antistreptavidin antibodies (Sigma) in pH 8.0 or pH 10.0 blocking buffer (100 μl/well). The plates were rinsed three times with 200 μl per well blocking buffer at the assay pH, incubated with secondary anti-IgG/alkaline phosphatase conjugate (Sigma) for 1 hr at room temperature, rinsed three times with blocking buffer, and assayed for alkaline phosphatase activity at pH 10.0. Every plate assayed had triplicates for each protein concentration. The data were processed on Mathcad (Mathworks) to determine the equivalent bulk concentration at 50% saturation of binding (EC$_{50}$) values using a published 4-parameter nonlinear fitting algorithm shown below (Jin et al., *J. Mol. Biol.* 226: 851–865 (1992)):

$$y=a+(d-a)/[1+\exp(b(c-x))]$$

where a, b, c, and d are the adjustable fitting parameters; x=streptavidin concentration (μg/ml); y=absorbance at 405 nm. Absolute EC$_{50}$ in μg ml$^{-1}$ are given by the value of the parameter c for the best fit of the fitting function to the binding isotherm. Relative EC$_{50}$ values reported in Table I are EC$_{50}$(mutant)/EC$_{50}$(WT streptavidin).

Equilibrium Binding of Biotin $^3$H-biotin at a concentration of 2 nM (WT, W79A, W120A) or 0.2 nM (WT, W120F) was incubated in aliquots of serially diluted protein for 2 h. The free ligand was then separated from the protein-bound ligand by either Microcon-30 or Centriprep-30 centrigual ultrafiltration devices (Amicon, Inc.). Typically, 0.1–1 ml of the free ligand solution or the protein-ligand mixture was added to 18 ml liquid scintillation cocktail (Ecolume, ICN Biomedicals, Inc., Costa Mesa, Calif.) and assayed on a liquid scintillation counter (Beckman Instruments, Inc., Fullerton, Calif.). The K$_a$ was determined from a nonlinear curve fit of the fraction of protein-bound ligand versus the free protein concentration.

Figure 2A:
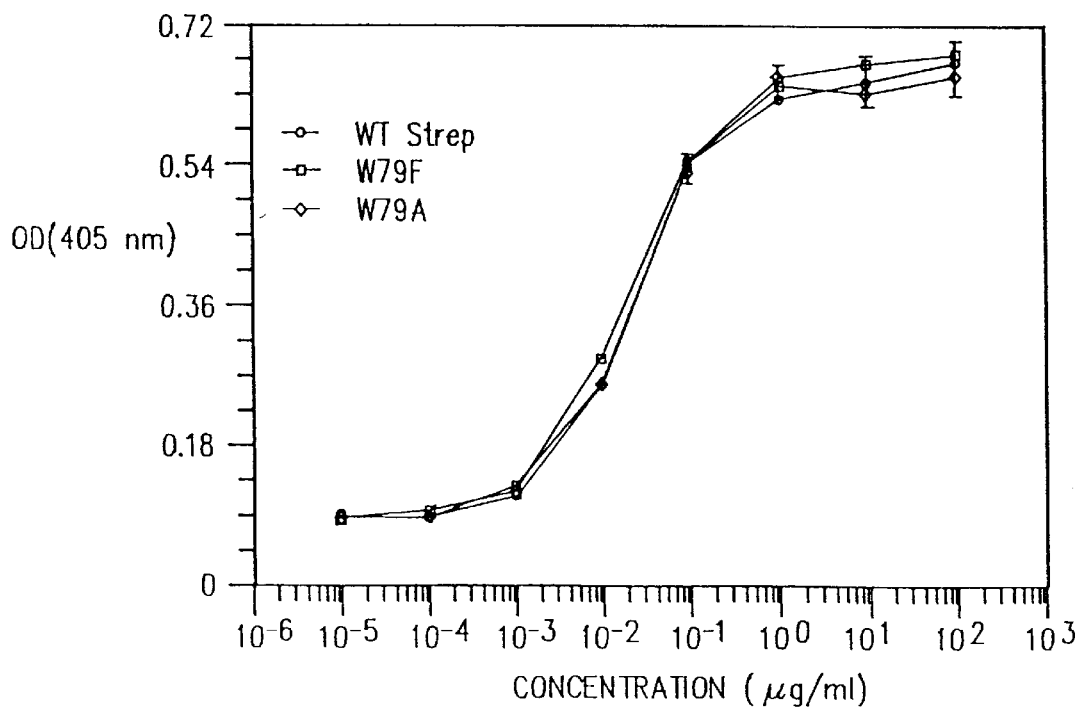
FIGS. 2A and 2B shows ELISA concentration-dependent binding of WT streptavidin, W79A, and W79F to (FIG. 2A) biotin/BSA at pH 10.0, (FIG. 2B) 2-iminobiotin/BSA at pH 10.0. Protein concentrations (tetramer) in μg/ml are plotted on the abscissa, while the alkaline phosphatase activity indicated by the absorbance at 405 nm are plotted on the ordinate.
Figure 2B:
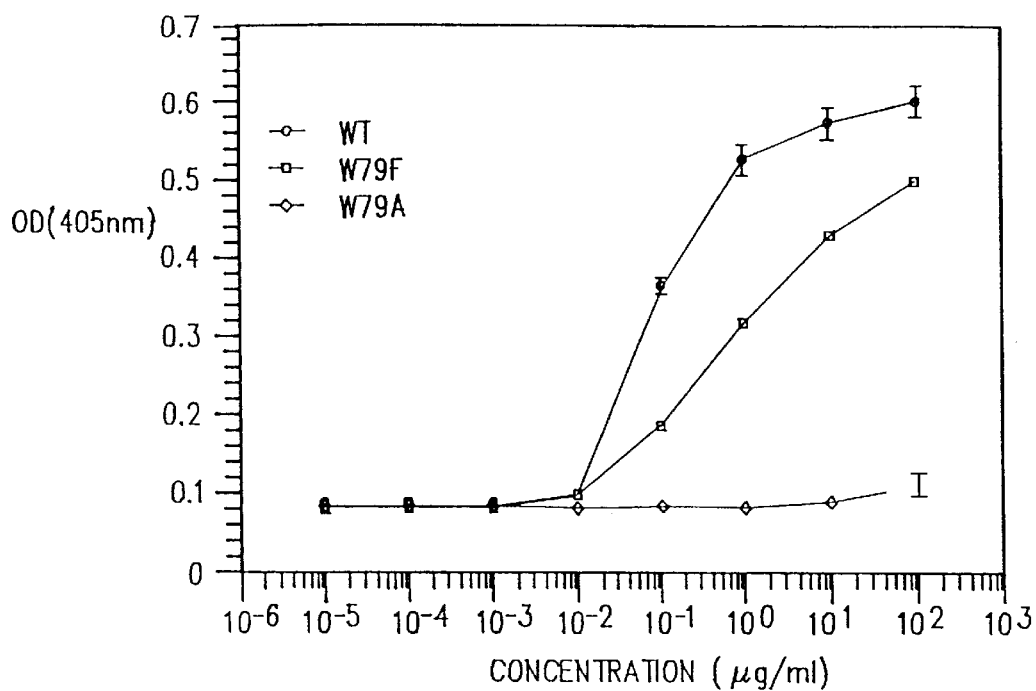

With biotin as the ligand, the concentration-dependent binding isotherms of WT streptavidin and all Trp mutants are largely identical in the ELISA assay at both pH 8.0 and 10 (FIG. 2A shows the binding isotherm of WT streptavidin and the W79A/F mutants). However, with iminobiotin/BSA as the ligand (FIG. 2B for WT streptavidin and the W79A/F mutants) the binding isotherms indicate marked differences in the affinities of WT streptavidin and the mutants, with the EC$_{50}$'s in the order WT<Phe<Ala. The absolute and relative EC$_{50}$ for the binding of the WT streptavidin and the Trp mutants to iminobiotin, at pH 8.0 and 10.0 are summarized in Table I and FIG. 2.

TABLE I

EC$_{50}$ results for binding of WT streptavidin and Trp mutants by 2-iminobiotin at pH 8.0 and pH 10.0

| Protein | pH | Absolute EC$_{50}$ (μg ml$^{-1}$) | Relative EC$_{50}$ (Mutant/WT) |
|---|---|---|---|
| WT* | 8/10 | 0.03 ± 0.02 | 1.0 |
| WT | 8 | 0.046 ± 0.03 | 1.0 |
| WT | 10 | 0.052 ± 0.013 | 1.0 |
| WxA** | 8/10 | ≧100 | ≧2000 |
| W79F | 8 | 8.27 ± 3.01 | 180 |
| W79F | 10 | 0.14 ± 0.01 | 2.7 |
| W108F | 8 | 9.6 ± 0.74 | 209 |
| W108F | 10 | 0.12 ± 0.07 | 2.3 |
| W120F | 8 | 10.27 ± 0.5 | 223 |
| W120F | 10 | 4.03 ± 1.91 | 78 |

The absolute EC$_{50}$ values (μg/ml$^{-1}$) were derived from the nonlinear least squares fit of at least three independent measurements of the binding isotherm. The relative EC$_{50}$ values are normalized to the average (absolute) EC$_{50}$ of WT streptavidin at pH 8 or pH 10, respectively.
*Biotin is the ligand. Six independent isotherms of WT binding to biotin/BSA were fitted to determine the EC$_{50}$.
**The complete binding isotherm off the Trp ->Ala mutants could not be determined, leading to a lower bound of their EC$_{50}$.

These experimental results indicated the Ala mutants were accessible for equilibrium biotin binding assays. A spin-column assay with a 30,000 MW cutoff filtration membrane was used to quantitate the partitioning of $^3$H-biotin between the free and bound states. This assay provides a useful estimate of the K$_a$ when the affinities lie between 10$^6$–10$^9$. The concentration-dependent binding isotherm for W120F was at the tight-binding limit (K$_a$>10$^9$) at the lowest experimentally accessible total biotin concentration (0.2 nM) and identical to wild-type streptavidin. While the W108A mutant protein proved to be unstable in this assay at the necessary concentrations, the W79A and W120A mutants yielded complete concentration-dependent binding isotherms from which the K$_a$ was determined to be 4.3×10$^7$ M$^{-1}$ and 8.6×10$^6$ M$^{-1}$, respectively. These experimentally determined K$_a$ estimates provide independent confirmation of the ΔK$_a$'s estimated from the ELISA assays as further discussed below.

Order of magnitude determinations of ΔK$_a$ for the mutants were estimated from the EC$_{50}$, given the known K$_a$'s of some of these ligand-protein partners. The subsequent analysis is based on the experimentally-determined K$_a$ of 2.5×10$^{13}$ M$^{-1}$ of biotin-WT streptavidin and the K$_a$ of =10$^8$ M$^{-1}$ for iminobiotin/WT streptavidin at pH 10.0, estimated from the experimentally-determined value for iminobiotin/avidin. These numbers are further supported by the independently determined biotin-binding affinities of the W79A and W120A mutants, which agree well with the ELISA estimates.

The ELISA assay is insensitive to the ΔK$_a$ in ligand-protein binding when the K$_a$ are higher than –10$^{7\,M}$–1, i.e., the ELISA binding isotherms for ligand-protein partners are indistinguishable when the K$_a$'s are in the range 10$^7$–10$^{13}$ M$^{-1}$. This assumption is supported by the following observations: the experimentally measured EC$_{50}$ for WT streptavidin/biotin is identical to the EC$_{50}$ of WT streptavidin/iminobiotin at pH 10.0, despite the marked differences in the K$_a$ of WT streptavidin/biotin (2.5×10$^{13}$ M$^{-1}$), and that of iminobiotin/WT streptavidin at pH 10.0 (~10$^8$ M$^{-1}$). The similar EC$_{50}$'s for these two ligands suggest that ELISA is generally insensitive to ΔK$_a$ in the range of 10$^8$–10$^{13}$M$^{-1}$. Furthermore, the binding of WT streptavidin by iminobiotin is pH-sensitive, and the K$_a$ of WT streptavidin/iminobiotin is likely to be an order of magnitude lower at pH 8.0 than at pH 10.0, as is the experimentally-determined $\Delta K_a$ for the closely related iminobiotin-avidin system. Thus, an upper limit of $10^7 M^{-1}$ for the sensitivity of ELISA towards ligand $K_a$ can be established. The similar biotin $EC_{50}$ values measured for WT streptavidin and all of the Trp mutants similarly suggests that the $K_a$ of the Trp mutants for biotin are in the $10^{7-1013} M^{-1}$ range.

Figure 3A:
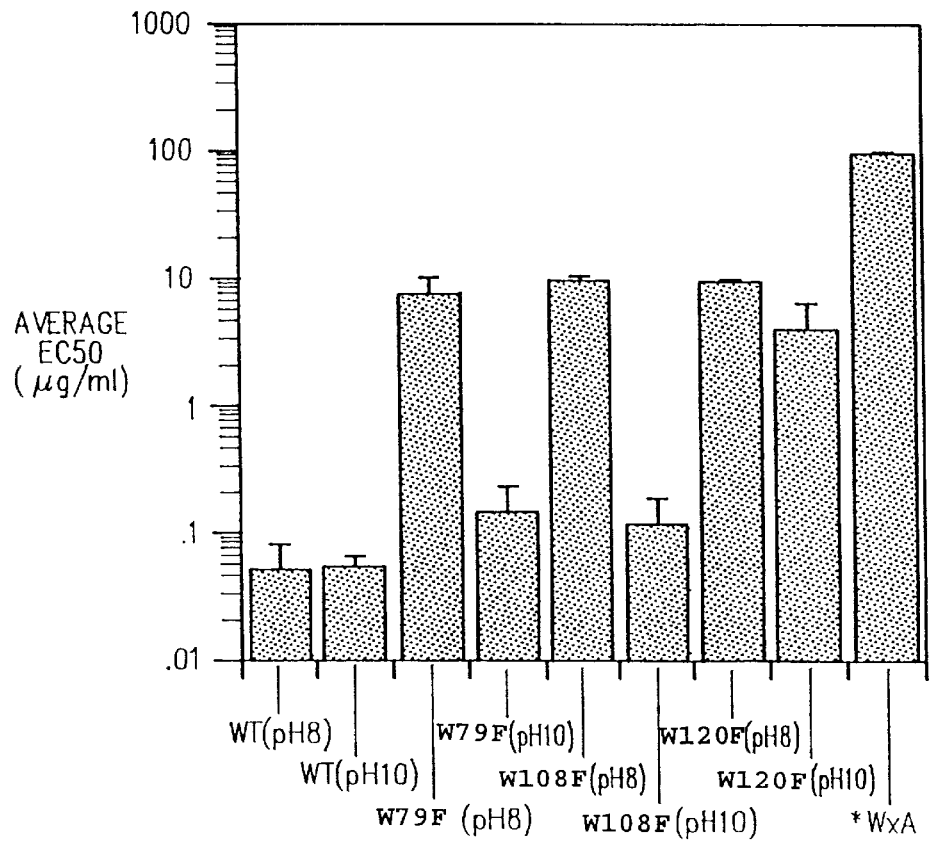
FIG. 3A shows average $EC_{50}$ values for the binding of WT streptavidin and Trp mutants to iminobiotin, at pH 8.0 and 10.0. Each mutant and its assay pH is identified on the abscissa, and the average $EC_{50}$ in μg ml$^{-1}$ is plotted on a logarithmic y-scale. The asterisk(*) on WxA indicates that the reported $EC_{50}$ is a lower bound, estimated from the (essentially) flat binding isotherm of the Trp->Ala mutants.
Figure 3B:
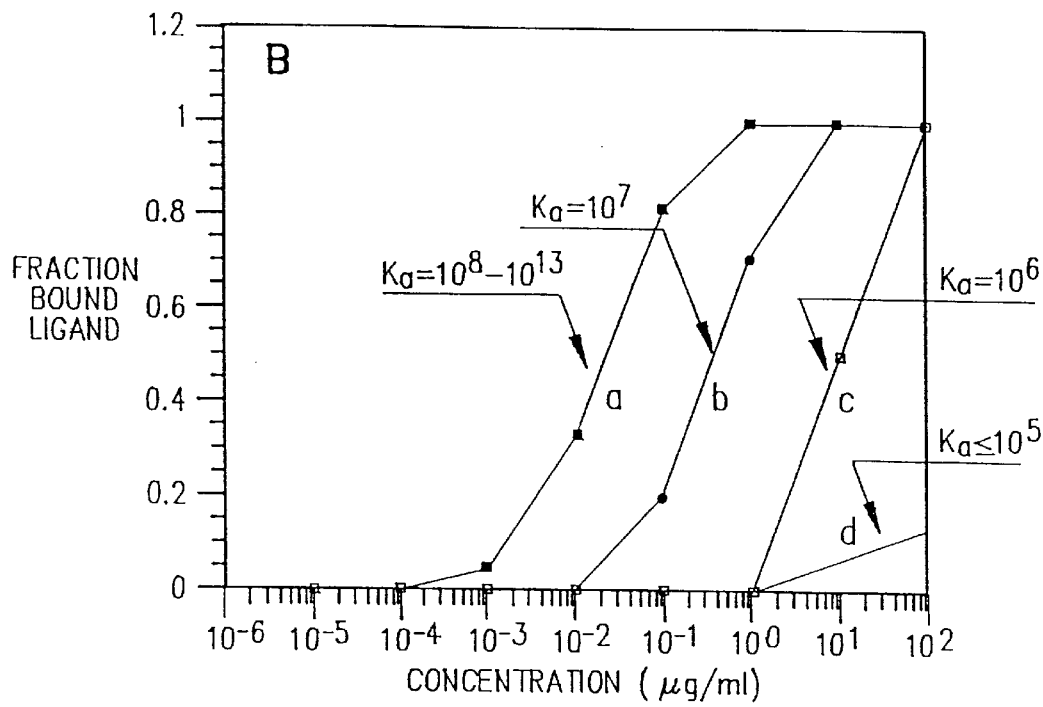
FIG. 3B shows ELISA binding isotherms calculated from the 4-parameter fitting function for characteristic values of absolute $EC_{50}$'s. Estimated $K_a$'s of iminobiotin-protein corresponding to each $EC_{50}$ are also shown.

However, when the ligand affinity is lowered into the accessible range of this ELISA assay by using iminobiotin as the ligand, marked changes in the $EC_{50}$'s are observed for the Trp mutants. The relative $EC_{50}$ results for the Trp mutants are summarized in FIG. 3, and illustrate their increased iminobiotin $EC_{50}$'s. W79F and W108F display ~2~3-fold greater $EC_{50}$'s at pH 10.0 compared to WT streptavidin; when the assay pH is lowered to 8.0, their $EC_{50}$'s dramatically increased by two orders of magnitude, consistent with the pH-dependent decrease in the affinity of iminobiotin for streptavidin. These results suggest that the affinity of W79F and W108F mutants for iminobiotin is less than one order of magnitude lower than WT streptavidin at pH 10.0 ($K_{a~107-108~M-1}$). Lowering the assay pH to 8.0 further decreases the $K_a$ to ~$10^6 M^{-1}$), compared to W79F and W108F, as shown by its 100-fold greater relative $EC_{50}$ at pH 10.0, and a weaker pH-dependence, shown by the smaller increase in relative $EC_{50}$ at pH 8.0 (relative $EC_{50}$~200 at pH 8).

Mutating Trp>Ala results in larger changes in 2-iminobiotin binding affinities, so that only a lower bound of their $EC_{50}$s can be estimated (relative $EC_{50} \geq 2000$). The $EC_{50}$'s for the Trp->Ala mutants bound to iminobiotin may be somewhat overestimated by a disproportionate loss of the bound protein during multiple washing steps in ELISA. Since the Ala mutants display a biotin-binding isotherm that is indistinguishable from that of WT streptavidin, which sets a maximum $\Delta K_a$, the $\Delta K_a$'s of the Ala mutants are estimated to fall between $10^4$-$10^6$. This result is supported by the direct estimation of $K_a$ for the W79A and W120A mutants, which places these affinities at $10^7 M^{-1}$.

The present analysis assumes that the $EC_{50}$ differences for iminobiotin reflect similar differences for biotin, which is supported by the calculations of Miyamoto and Kollman, that the difference in the absolute free energies of binding for the two ligands are largely due to the differences in the solvation energies of the two ligands rather than large differences in ligand-protein interaction free energies (Miyamoto and Kollman, *Proteins* 16: 226–245 (1993), and Miyamoto and Kollman, *Proc. Natl. Acad. Sci. USA* 90: 8402–8406 (1993)). The $\Delta K_a$ estimates from the 2-iminobiotin ELISA binding isotherms are closely corroborated by the direct estimates of the biotin $K_a$ for the W79A, W120A and W120F mutants. Iminobiotin is thus a good reporter for intrinsic streptavidin-biotin interactions, consistent with the fact that the tryptophans do not directly interact with the structurally altered ureido moiety.

These results, and notably the ranking of affinities in the order of the aromaticity of the side chains Trp (WT) >Phe>Ala and the associated magnitude of the changes in the $EC_{50}$ for binding to iminobiotin, indicate that altering the aromatic content of the contact residues greatly -impacts the absolute free energy of binding. Thus, partial retention of side chain aromaticity by altering Trp to Phe results in a $10^1$-$10^2$ increase in iminobiotin $EC_{50}$'s, which is indicative of a similar decrease in their $K_a$ for biotin. Complete abolition of the aromatic side chain by mutating Trp to Ala results in considerably greater $EC_{50}$'s, which is indicative of a $\Delta K_a$ (biotin) ~$10^3$ lower than WT streptavidin. These results suggest that the contribution of a Trp side chain to the absolute free energy of biotin binding could be as much as ~4 kcal/mol; since four Trp residues contact biotin, their overall contribution to the absolute free energy of binding biotin is substantial.

The equilbrium binding enthalpies, $\Delta H°$, and the heat capacities, $\Delta Cp°$, have also been engineered with the streptavidin mutants (Table II). Heat capacities were determined as generally described in Murphy et al., *Proteins: Structure, Function and Genetics* 15:113–120 (1993), incorporated herein by reference. As can be seen, there are examples of both increased and decreased $\Delta H°$ and increased and decreased $\Delta Cp°$. The heat capacities relate the temperature dependence of the binding enthalpy, which contributes significantly to the binding affinity. Alterations in the heat capacity are thus important in applications where temperature is used as a variable to control the biotin affinity.

TABLE II

| Protein | $\Delta H°$ (kcal/mol) | $\Delta Cp°$ (cal/molK) |
|---------|------------------------|--------------------------|
| WT      | −24.5                  | −345                     |
| W79A    | −18.5                  | −357                     |
| W79F    | −25.9                  | −266                     |
| W108F   | −23.5                  | −386                     |
| W120F   | −19.4                  | −303                     |
| W120A   | −12.8                  | −272                     |

EXAMPLE II

This Example demonstrates the contribution of binding-site tryptophan residues to the biotin off rate and activation thermodynamics. The dissociation rate constants of streptavidin mutants W79F, W108F and W120F indicate these Trp contacts are important in regulating the dissociation rate.

The streptavidin-biotin dissociation rate was determined for WT streptavidin, W79F, W108F, and W120F as follows. 8,9-$^3$H biotin (4.8 $\mu$l, 21 $\mu$M, NEN/Dupont) was added to 10 ml PBS, pH 7.4, 1 mM EDTA, containing WT streptavidin or one of W79F, W108F or W120F mutants at a concentration of 0.5 $\mu$M and incubated for 10 min followed by addition of non-radioactive biotin (20 mM) to a final concentration of 50 $\mu$M. Aliquots (0.5 ml) of this mixture were centrifugally ultrafiltered through a 30,000 MW cutoff filter (Microcon-30, Amicon Inc., Beverly, Mass.) to separate the unbound biotin from the protein-ligand complex. Fifty $\mu$l of the filtrate were mixed with 10 ml scintillation cocktail in triplicate and assayed for radioactivity in a liquid scintillation counter (LS-7000, Beckman Instruments, Fullerton, Calif.). The average radioactivity of the filtrate in cpm at each time point and radioactivity of the protein-ligand complex before addition of cold biotin (a) allowed the first order rate constant of the dissociation of protein-ligand complex ($k_{off}$) to be determined from the plot of ln(a−x/a) [ln(fraction bound)]. Standard deviations were determined based on three independent measurements. Control experiments where no cold biotin was added yielded <2% of the total radioactivity in the ultrafiltrate, demonstrating that all $^3$H biotin was initially bound.

Figure 4A:
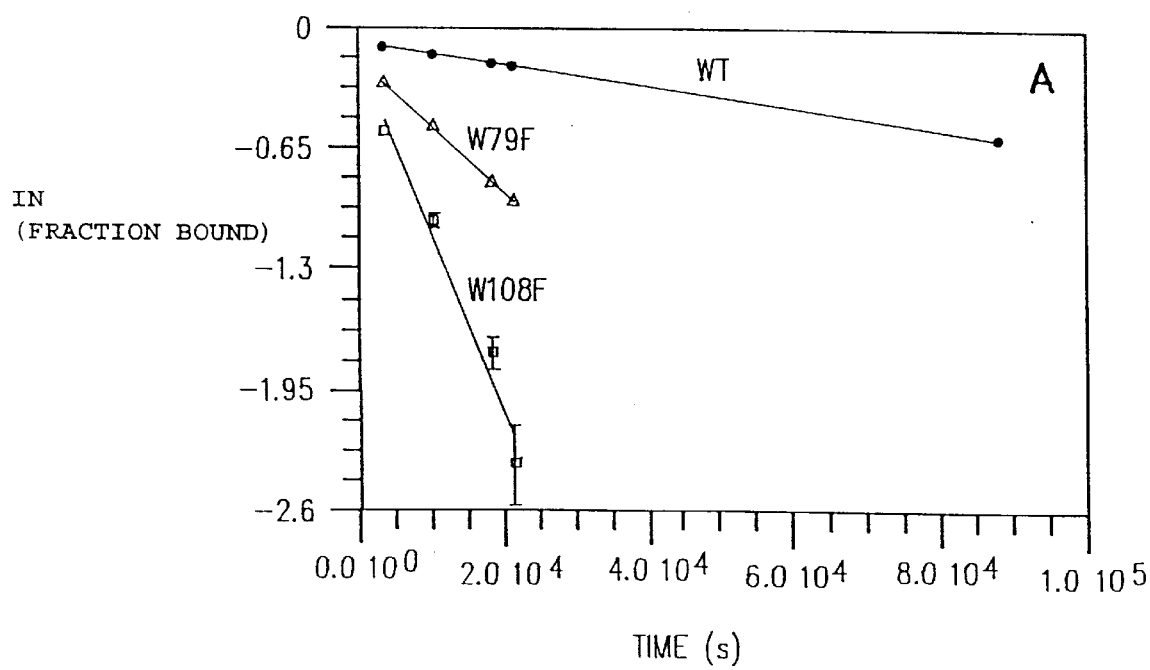
FIG. 4A and FIG. 4B show the streptavidin-biotin dissociation rate at 298 K, where
Figure 4B:
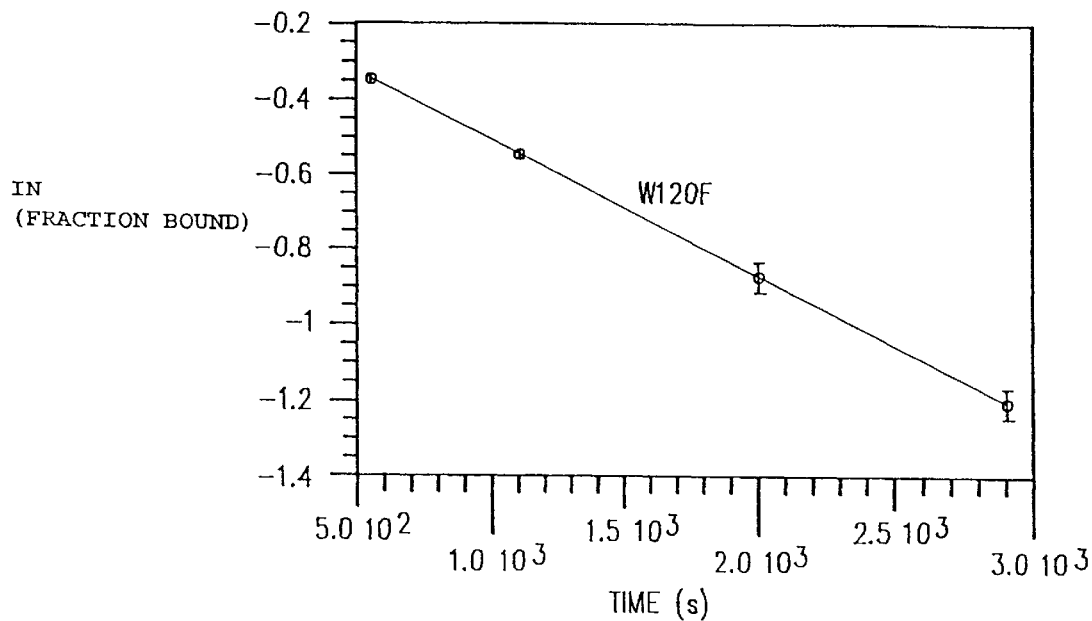

The results, as shown in FIG. 4, indicate that biotin-bound wild-type (WT) core streptavidin and the site-directed mutants W79F, W108F, and W120F display monoexponential, first order, dissociation kinetics. The first order dissociation rate constants ($k_{off}$) are summarized in Table III. The $k_{off}$ of recombinant core WT streptavidin ($k_{off}$=5.6×10$^{-6}$ s$^{-1}$) is approximately twice that reported earlier for a commercial preparation of full length streptavidin (Piran and Riordan, *J. Immunol. Meths.* 133:141–143 (1990), although monophasic dissociation kinetics were obtained for the recombinant core WT streptavidin as opposed to the multiphasic kinetics observed with commercial preparations of streptavidin.

TABLE III

The rate constant for the dissociation of biotin-protein complex ($k_{off}$), relative dissociation rate constant ($\Delta k_{off}$), and relative equilibrium dissociation constant ($\Delta K_d$) for WT streptavidin and W79F, W108F, and W120F mutants at 298 K. $\Delta k_{off}$ and $\Delta K_d$ are defined relative to WT streptavidin.

| Protein | $k_{off}(S^{-1})$ | §$\Delta k_{off}$ | †$\Delta K_d$ |
|---|---|---|---|
| WT | $5.4 \times 10^{-6}$ | 1 | 1 |
| W79F | $3.6 \times 10^{-5}$ | 5.5 | ~$10^1$ |
| W108F | $9.6 \times 10^{-5}$ | 17 | ~$10^1$ |
| W120F | $3.7 \times 10^{-4}$ | 70 | ~$10^2$ |

§$\Delta k_{off} = k_{off}(\text{mutant})/k_{off}(\text{WT})$
†$\Delta K_d = K_d(\text{mutant})/K_d(\text{WT})$ The effects of replacing the Trp residues in contact with biotin by Phe were significant and position-dependent. There was a dramatic effect in the $k_{off}$ upon replacing Trp 120 with Phe: the conservative W120F mutation resulted in a 70-fold increase in the dissociation rate constant, relative to WT streptavidin, corresponding to a decrease in the $t_{1/2}$ from 35 h (WT) to 0.5 h (W120F). The effects of replacing Trp with Phe at positions 79 and 108 were also significant, though smaller in magnitude. The $k_{off}$ for W79F was 5-fold greater, and that of W108F was 17-fold greater than WT streptavidin. The $\Delta k_{off}$ of W79F and W120F relative to WT streptavidin, summarized in Table I, were similar in magnitude in their $\Delta K_d$, suggesting that the decreased equilibrium affinity of W79F and W120F can be largely accounted for by their increased $k_{off}$. W108F, on the other hand, displayed a biotin $\Delta k_{off}$ that is larger than the $\Delta K_d$, suggesting that the corresponding on-rate alterations also exist. These results indicate that the alterations in the off rate kinetics for W79F and W120F are largely accounted for by a free energy destabilization of the ligand-bound ground state relative to WT streptavidin, while stabilization of the transition state of W108F relative to WT largely accounts for the $\Delta k_{off}$ of this mutant.

The energetic origins of the marked differences in $k_{off}$ for W79F, W108F, and W120F were further examined by measuring the temperature-dependence of the dissociation rates, and applying transition state theory to determine the enthalpic and entropic contributions to the activation barrier. The activation thermodynamic parameters, calculated with the assumption of a single transition state, are summarized in Table IV. The exceptionally slow biotin off-rate is due to a large activation barrier, $\Delta G_r^{\neq}=24.4$ kcal mol$^{-1}$, for biotin dissociation. The activation barrier is enthalpic in origin, $\Delta H_r^{\neq}=+32$ kcal mol$^{-1}$, with a positive activation entropy of 7.6 kcal mol$^{-1}$ at 298 K. An unexpected finding is that both W79F and W108F exhibit a larger activation enthalpy of dissociation (+3,+4.5 kcal mol$^{-1}$) compared to WT streptavidin. However, this Trp->Phe substitution results in an even larger positive increase in the activation entropy contribution, as the $T\Delta S_r^{\neq}$ term for W79F and W108F favors dissociation by 4–6 kcal mol$^{-1}$ at 298 K. In direct contrast, the 70-fold faster off-rate of W120 (corresponding to a $\Delta\Delta G_r^{\neq}$ of −2.1 kcal mol$^{-1}$ relative to WT streptavidin) largely arises from a decreased activation enthalpic barrier ($\Delta H_r^{\neq}=+28.5$ kcal mol$^{-1}$), with an activation entropy that is very similar to WT streptavidin.

TABLE IV

Thermodynamic parameters derived from transition state analysis of the temperature-dependent dissociation of the biotin-streptavidin (WT or mutant) complex.

| Protein | $\Delta H_r^{\neq}$ (kcal mol$^{-1}$) | $^1 T\Delta S_r^{\neq}$ (kal mol$^{-1}$) | $\Delta G_r^{\neq}$ (kal mol$^{-1}$) | $^2\Delta\Delta G_r^{\neq}$ (kal mol$^{-1}$) |
|---|---|---|---|---|
| WT | 32.0 ± 2.1 | 7.6 ± 2.1 | 24.4 ± 2.4 | 0 |
| W79F | 34.9 ± 0.6 | 11.6 ± 0.6 | 23.3 ± 0.8 | −1.1 |
| W108F | 36.5 ± 0.9 | 13.8 ± 0.9 | 22.7 ± 1.3 | −1.7 |
| W120F | 28.5 ± 1.0 | 6.6 ± 1.0 | 21.9 ± 1.4 | −2.5 |

$^1 T = 298K$
$^2\Delta\Delta G_r^{\neq} = \Delta G_r^{\neq}(\text{mutant}) - \Delta G_r^{\neq}(\text{WT})$ The determination of $\Delta G_r^{\neq}$ by transition state analysis and the independent estimation of $\Delta G^0$ from affinity measurements allows the drawing of free energy profiles for WT streptavidin and the Trp to Phe mutants. Similarly, the enthalpic energy profiles can be drawn from the equilibrium biotin-binding enthalpy ($\Delta H^0$), independently determined by isothermal titrating calorimetry measurements, and $\Delta H_r^{\neq}$ available from transition state analysis of the temperature-dependent protein-ligand dissociation kinetics. The virtue of this analysis is that is allows the free energy barriers responsible for the off-rates of the different mutants to be delineated in terms of alterations in the transition state and/or the biotin-bound ground state, and further partitions these free energy changes into enthalpic and entropic components. Upon comparison with the results for WT streptavidin, the thermodynamic effects of mutating specific residues can then be mapped, providing considerable insight into the structure and energetics of the transition state.

Turning to the free energy profiles for WT streptavidin and the Trp to Phe mutants, the 70-fold decrease in the $k_{off}$ of W120F is believed due to the destabilization of its biotin-bound ground state relative to WT streptavidin, $\Delta\Delta G=+2.7$ kcal mol$^{-1}$ vs. $DDG_r\pi=-2.5$ kcal mol$^{-1}$. This alteration in the free energy of the ligand-bound state upon mutating Trp120 to Phe is enthalpically controlled, $\Delta\Delta H^0=+5.1$ kcal mol$^{-1}$, with a favorable entropy term, $TDDS\infty=+2.4$ kcal mol$^{-1}$. W79F displays the smallest decrease in the $k_{off}$, which can also be attributed to the destabilization of the biotin-bound ground state. The origin of this +0.9 kcal mol$^{-1}$ $\Delta\Delta G^0$ term is different from W120F. The change in equilibrium binding enthalpy actually favors association since $\Delta\Delta H^0=-1.5$ kcal mol$^{-1}$, indicating that the free energy destabilization of the biotin-bound state caused by mutating Trp70 to Phe is caused by an even larger unfavorable entropic alteration, $T\Delta\Delta S^0=-2.4$ kcal mol$^{-1}$.

EXAMPLE III

This Example demonstrates that streptavidin-biotin equilibrium affinity and dissociation kinetics engineered by site-directed mutagenesis allow efficient capture of a biotinylated target molecule while subsequently allowing dissociation of the streptavidin-biotinylated target complex under non-denaturing conditions by exploiting competitive dissociation with free biotin. The ability to tailor the biotin-binding affinity and dissociation kinetics is used to create chimeric streptavidin tetramers composed of subunits with widely differing affinities and biotin off rates.

Figure 5A:
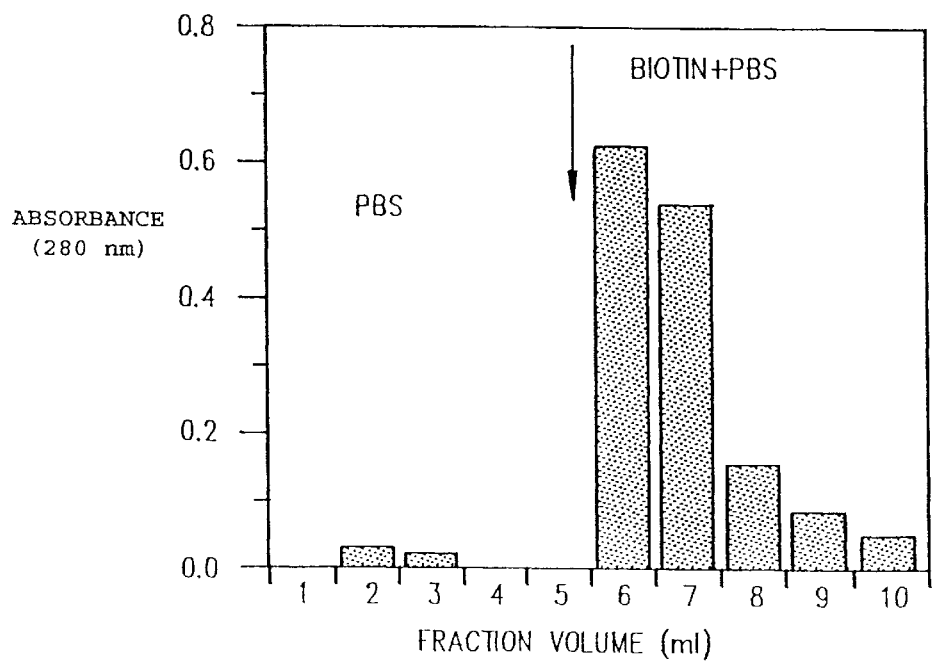
FIG. 5A shows the binding of W120A and FIG. 5B shows the binding of WT streptavidin to a biotin column and subsequent elution with 2 mM biotin.
Figure 5B:
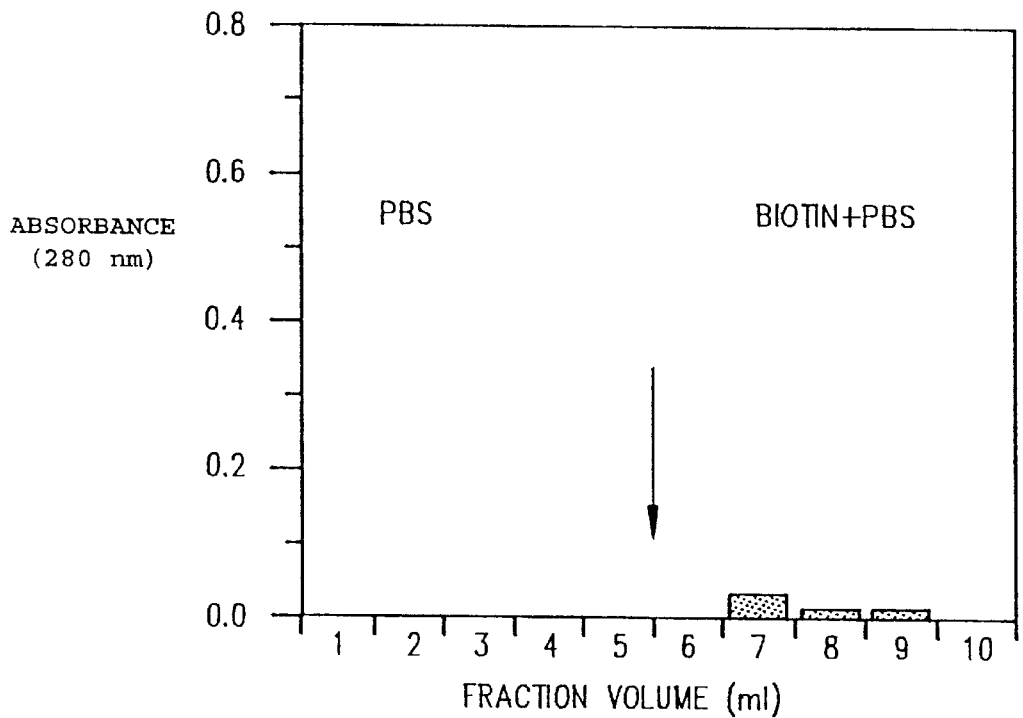

The Trp120->Ala (W120A) mutant (Example I), which has a $K_a$ of $10^7$ M$^{-1}$ and a $k_{off} \leq 10^{-2}$ s$^{-1}$ was used to demonstrate the reversible separation of a biotinylated molecule. W120A binds to a biotinylated chromatography support under buffer flow, and can be subsequently eluted with 2 mM biotin (FIG. 5A). The experiment was performed as follows: 0.4 mg of W120A in PBS, pH 7.4 was added to a 1 ml biotin-functionalized column (Sigma Chemicals, St Louis, Mo.). The column was washed with 5 ml PBS to remove nonspecifically adsorbed protein, followed by elution with 2 mM biotin in PBS. All of the added W120A was recovered in the biotin elute as determined by optical absorbance at 280 nm. An identical experiment with WT streptavidin resulted in irreversible binding of the protein to the column which could not be eluted by biotin (FIG. 5B), even after incubation of the column in strong denaturants, which is consistent with the exceptional stability of biotin-bound streptavidin. The initial binding of W120A and WT streptavidin to an immobilized biotin column is a consequence of their high affinity. Upon subsequent addition of biotin to the buffer flow, the fast off rate of the W120A-biotin complex allows effective competition of the free biotin for the immobilized (column bound) biotin, leading to displacement of bound W120A. In the case of WT streptavidin, the extremely slow biotin off rate ($t_{1/2}$=35 h) precludes the dissociation of the immobilized biotin-WT streptavidin, resulting in essentially irreversible binding of the protein to the column.

The fast off-rate kinetics of W120A also permitted regeneration of ligand-free protein by ultrafiltration or dialysis. The reverse experiment, the binding of biotinylated target to immobilized W120A, and subsequent elution with free biotin is equivalent to this experiment. The binding of W120A to immobilized biotin, and its elution with free biotin, and the irreversible binding of WT streptavidin, highlights the importance of controlling both the affinity and off-rate kinetics in the optimization of affinity separations.

Figure 6A:
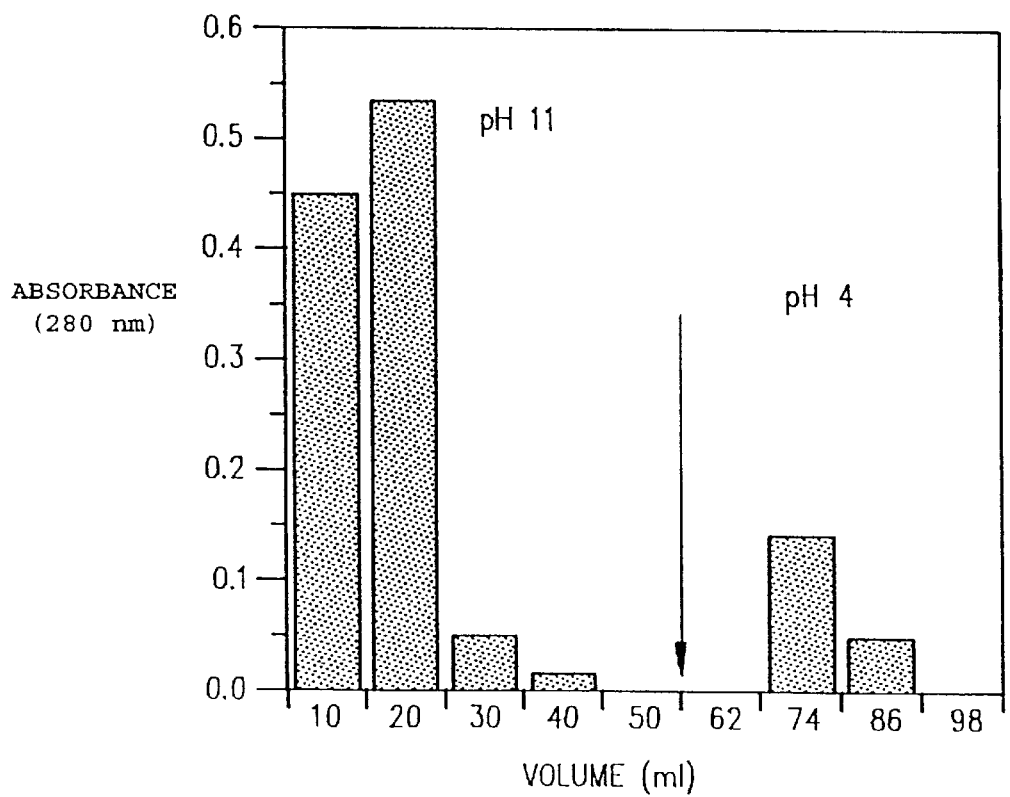
FIG. 6A and FIG. 6B show the purification of chimeric streptavidin tetramers.
Figure 6B:
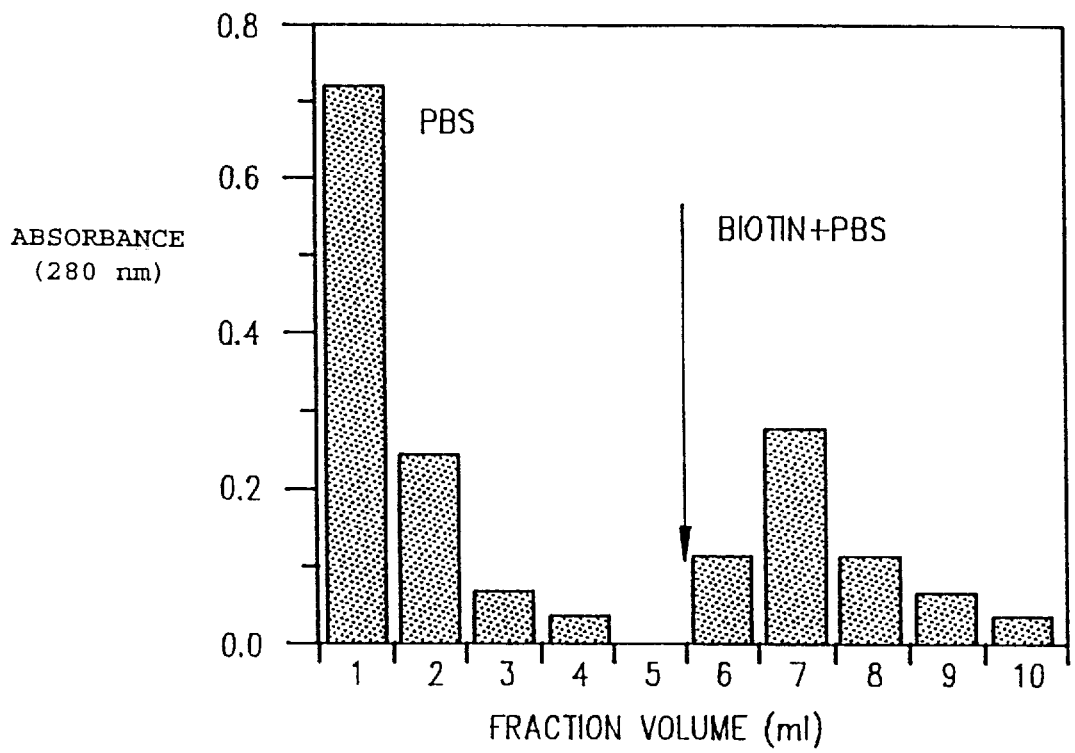
Figure 7A:
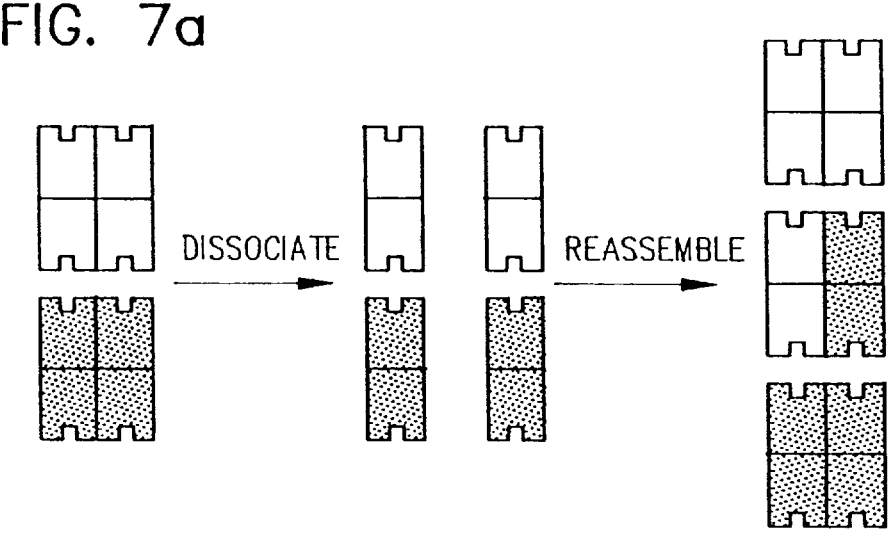
FIG. 7A is a schematic illustration of dissociation across the dimer/dimer interface with subsequent reassembly of heterodimeric tetramers. The shading denotes a tetramer with non-identical compositions, e.g. mutant binding sites, different fluorescent labels, conjugated drug, etc.
Figure 7B:
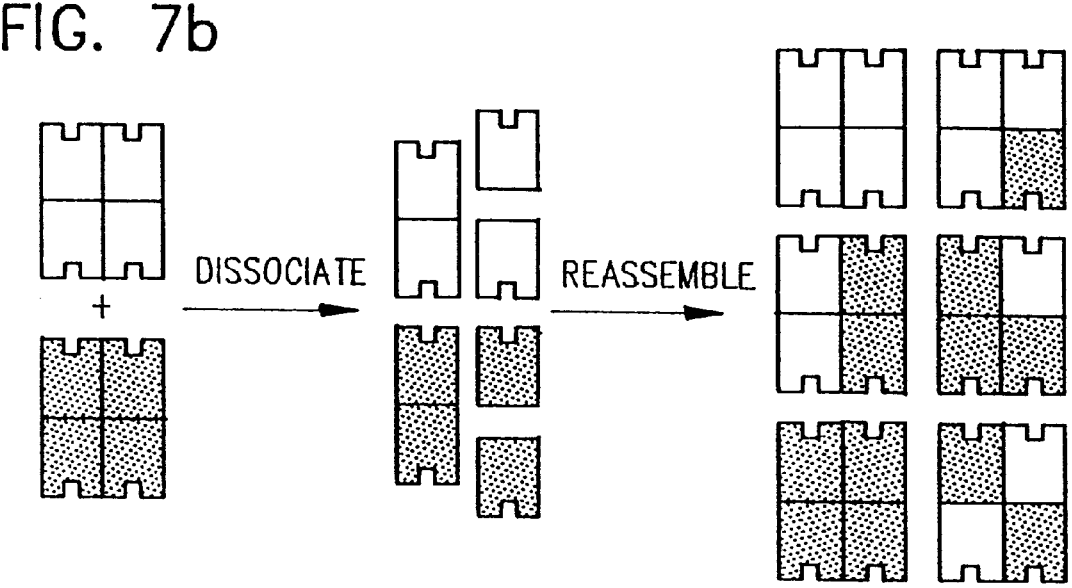
FIG. 7B shows a schematic illustration of dissociation across both the dimer/dimer and monomer/monomer interfaces so that both dimer and monomer intermediate species are present. Subsequent reassembly results in a collection of chimeric tetramer species.

Chimeric tetramers with mixed WT streptavidin and W120A subunits were created by mixing equimolar amounts of WT streptavidin and W120A, denaturation in guanidine thiocyanate, followed by slow renaturation of the denatured protein by dialysis, as follows: 2.4 mg each of WT streptavidin and W120A (protein volume=1.13 ml) were incubated in 7.6 ml, 6M guanidine thiocyanate for 1 h at room temp, and dialyzed overnight in 4 L 25 mM Tris.Cl, 80 mM glycine at 4° C. The dialysate was then recovered for further purification. Upon refolding, a number of distinct protein populations result: chimeric tetramers with subunit stoichiometries of 1:3. 2:2 and 3:1 (WT:W120A), parent WT and W120A, and denatured protein subunits caused by aggregation/misfolding. The separation of the chimeric tetramers from parent W120A tetramers and misfolded/aggregated protein utilized 2-iminobiotin affinity chromatography. W120A exhibits <$10^3$ $M^{-1}$ affinity for 2-iminobiotin. Passage of the dialysate over an iminobiotin column, and elution of bound protein at pH 4, resulted in the recovery of ~20% of the original protein, consisting of chimeric tetramers and parent WT streptavidin (FIG. 6A). The dialysate was equilibrated in binding buffer (50 mM sodium carbonate, 0.5 M NaCl, pH 11) and passed over a 10 ml iminobiotin column (Pierce, Rockford, Ill.). Unbound protein (~4 mg) was eluted in binding buffer, and specifically bound protein (0.8 mg) was eluted in 50 mM sodium acetate, 0.5 M NaCl, pH 4. The recovered protein was concentrated, and exchanged into PBS, pH 7.4 by diafiltration. The separation of chimeric tetramers from parent WT streptavidin used the vastly differing biotin off rates of WT streptavidin and W120A. The protein was incubated with ~2-fold excess of biotin, and exhaustively ultrafiltered to remove the excess biotin. Since the $t_{1/2}$ of WT-biotin complex is 35 h, while that of W120A is <$10^2$ s, this results in the removal of biotin from a substantial fraction of W120A biotin-binding sites as well. The protein was then passed over a biotin column, washed with buffer, and then eluted with 2 mM biotin (FIG. 6B). Parent WT streptavidin tetramers saturated with biotin did not bind to the column, while WT streptavidin tetramers with free biotin-binding sites bind irreversibly to the biotin column (cf. FIG. 5B). This step effectively separates the chimeric tetramers from the parent WT streptavidin tetramers.

Protein-containing fractions eluted with biotin migrated similarly to biotin-bound streptavidin tetramers in native polyacrylamide gel electrophoresis, indicating similar quaternary structure (20 $\mu$l of the mixed tetramers at $\mu$M concentration were analyzed on a 8% acrylamide gel in the absence of SDS on a Miniprotean gel electrophoresis apparatus (BioRad Inc., Hercules, Calif.)). Direct corroboration that the protein population was composed of chimeric tetramers was obtained by electrospray mass spectrometry (ESMS). The chimeric streptavidin tetramers were analyzed by ESMS under conditions that favor preservation of non-covalent association. Protein concentrations (WT+biotin, W120A and mixed tetramers) were 10–50 $\mu$M tetramer in 10 mM ammonium acetate, pH 8.6. Experiments to detect the tetrameric charge states were conducted on a low frequency extended mass range single quadrupole mass spectrometer (Extrel Corp.). Instrument details and general operating conditions can be found in Light-Wahl et al., *J. Amer. Chem. Soc.* 115:5869 (1993); Light-Wahl et al., *J. Amer. Chem. Soc.* 116: 5271 (1994); Schwartz et al., *J. Amer. Soc. Mass Spectrom.* 5:201–204 (1994); and Schwartz et al., *J. Amer. Soc. Mass Spectrom.*, in press (1995), incorporated herein by reference. The results are shown in Table V.

TABLE V

ESMS results of protein eluted by buffer and biotin in biotin chromatography of mixed tetramers. Biotin eluted protein corresponds to FIG. 6B, while buffer eluted protein corresponds to FIG. 6B.

| Sample | Charge State | Centroid (m/z) | FWHM (m/z) | Intensity (counts) | Mass (Da) |
|---|---|---|---|---|---|
| Biotin eluted protein | +15 | 3555 | 95 | 2376 | 53353 ± 43 |
|  | +14 | 3815 | 110 | 4123 |  |
| Buffer eluted protein | +15 | 3580 | 90 | 3586 | 53751 ± 66 |
|  | +14 | 3845 | 90 | 2920 |  |
| WT tetramers | +15 | 3540 | 75 | 4897 | 53136 ± 51 |
|  | +14 | 3800 | 60 | 3808 |  |

Both the shifted peak position of the +14 and +15 charge state (indicative of tetrameric streptavidin) of the putative chimeric tetramer, and its greater full width at half maximum (FWHM) in comparison with the position and FWHM of parent WT+biotin or W120A tetramers (Table VI) is consistent with the presence of chimeric tetramers comprising biotin-bound WT and biotin-free W120A subunits. The alternative explanation, that the shift in position of the +14 charge state and broader FWHM could arise from a mixed population of biotin-bound WT and W120A tetramers is precluded by the affinity purification employed.

TABLE VI

Calculated m/z values for tetrameric charge states for different stoichiometric association of W120A subunits and WT + biotin subunits.

| Sample | Calculated m/z | | |
|---|---|---|---|
| | +15 | +14 | Mass (Da) |
| W120A | 3510 | 3760 | 52624 |
| W120A:WT + biotin (3:1) | 3535 | 3785 | 52983 |
| W120A:WT + biotin (2:2) | 3555 | 3810 | 53342 |
| W120A:WT + biotin | 3580 | 3835 | 53701 |
| WT + biotin | 3605 | 3860 | 54060 |
| WT | 3540 | 3795 | 53084 |

Further corroboration that both WT subunits and W120A subunits were present in this protein was obtained by analyzing the protein under conditions that favored dissociation of the tetramer into monomers. The ESMS experiment to detect monomeric ions was conducted on a FinniganMAT triple quadrupole mass spectrometer under capillary heating conditions that lead to dissociation of the tetramer into +6 and +7 monomeric ions (capillary voltage=+2.7 kV, capillary temperature=180° C.); sample preparation was as described above. These ESMS results indicated that the peaks associated with the +7 and +6 charge state arose from both WT and W120A subunits.

The subunit mixing of two distinct populations of a multisubunit protein was demonstrated by resonance energy transfer experiments where one population was labeled with a fluorescence energy donor and the other with a complementary fluorescence energy acceptor, as generally described in Erijman and Weber, *Biochemistry* 30: 1595–1599 (1991), and Erijman and Weber, *Photochem. Photobiol.* 57: 411–415 (1993), incorporated herein by reference. Equimolar amounts of fluorescein isothiocyanate-labeled WT streptavidin (FITC-WT streptavidin) and 7-diethylamino-3-(4'-isothiocyanatophenyl)-4-methylcoumarin-labeled WT streptavidin (CPI-WT streptavidin) were mixed, denatured in 6 M guanidine isothiocyanate, and allowed to renature by dialysis in buffer, as follows: WT streptavidin was labeled with FITC or CPI (Molecular Probes, Eugene, Oreg.) by incubating protein in a ten-fold molar excess of FITC or CPI in 50 mM $Na_2CO_3$, 150 mM NaCl, pH 9.0, for 2 h at room temp. The labeled proteins were then separated from unbound fluorophore by gel filtration (PD-10, Pharmacia, Piscataway, N.J.). Fluorophore labeling ratios were typically 3–4 per tetramer as determined by optical absorbance measurements. Equimolar mixtures of FITC-labeled WT streptavidin and CPI-labeled WT streptavidin were incubated in 1.5 ml 6M guanidine thiocyanate for 1 h at room temp, and then dialyzed against 25 mM Tris.Cl, 80 mM glycine, pH 8.6. Fluorescence measurements were performed on a Hitachi F-5000 spectrofluorimeter: excitation=385 nm, emission=400–500 nm. While care was taken to ensure identical concentration of the renatured protein tetramers and the control, dilution effects arising from dialysis were corrected for by normalization to the tryptophan fluorescence of each sample.

Thus, upon physical mixing of these two distinct tetrameric populations, followed by chaotrope-induced denaturation and protein refolding, the occurrence of resonance energy transfer clearly demonstrated the creation of chimeric tetramers, consisting of two different subunit types. The results with WT streptavidin are shown in FIG. 1: The emission spectrum of the renatured mixture displayed a significant enhancement in the intensity of FITC-labeled WT streptavidin, the fluorescence energy acceptor, compared to a mixture of these two labeled proteins that had not undergone denaturation/renaturation, indicating the occurrence of fluorescence energy transfer. The observation of fluorescence resonance energy transfer is diagnostic of the presence of donor and acceptor labels on the same (tetrameric) molecule, a consequence of the creation of chimeric streptavidin tetramers consisting of subunits of both FITC-labeled WT streptavidin and CPI-labeled WT streptavidin.

These results demonstrate that a targeting component (biotin bound to WT subunits) and an imaging component (binding of the chimeric streptavidin tetramer to a biotin column by W120A subunits) can be separated by the use of chimeric streptavidin tetramers with different subunit affinities and biotin-dissociation kinetics. Thus, for drug delivery, imaging, and other such uses, the chimeric tetramer is loaded with a biotinylated molecule (e.g., biotinylated antibody) such that it is selectively partitioned to the high affinity subunits by virtue of the fast off-rate of the lower affinity subunits. The biotinylated target/chimera complex is targeted to the desired site via the antibody. The imaging agent or drug is circulated and captured by the lower affinity subunits.

Although the foregoing invention has been described in some detail by way of illustration and example for purposes of clarity of understanding, it will be obvious that certain changes and modifications may be practiced within the scope of the appended claims.

What is claimed is:

1. An isolated chimeric streptavidin tetramer comprising between one and three modified monomers,
   wherein the tetramer is formed by mixing wildtype monomers and a single type of modified monomer,
   wherein the chimeric tetramer has one or more of the following characteristics:
   (i) an overall altered binding affinity for biotin or a compound comprising biotin wherein a subunit modification consists of either a substitution of a hydrophobic amino acid for one or more amino acids present in the biotin binding domain or a deletion of one or more amino acids in the biotin binding domain,
   (ii) an altered subunit affinity conferring an enhanced sensitivity to hydrostatic pressure wherein a subunit modification consists of the substitution of an amino acid selected from the group consisting of a positively-charged amino acid, a negatively charged amino acid, or a cysteine for an amino acid present either in the region of a monomer-monomer interface or in the region of the dimer-dimer interface, and
   (iii) a molecular label permitting monitoring of subunit association into tetramers having specific stoichiometric ratios of modified and unmodified subunits wherein a subunit modification consists of the substitution of cysteine for asparagine at amino acid position 94 and covalent attachment of the label to the cysteine, and,
   (iv) a capacity to bind to a molecule other than streptavidin, biotin, or a compound comprising biotin, wherein a subunit modification consists of the substitution of cysteine for asparagine at amino acid position 94 and covalent attachment of the molecule to the cysteine.

2. The chimeric streptavidin tetramer of claim 1, wherein the streptavidin tetramer has an overall altered binding affinity for biotin or a compound comprising biotin wherein a subunit modification consists of either a substitution of a hydrophobic amino acid for one or more amino acids present in the biotin binding domain or a deletion of one or more amino acids in the biotin binding domain.

3. The chimeric streptavidin tetramer of claim 1, wherein the modified monomer further comprises a label, linker, drug, toxin, targeting molecule, metal, or enzyme.

4. The chimeric streptavidin tetramer of claim 1, wherein the subunit modification consists of the substitution of a cysteine for an amino acid present either in the region of a monomer-monomer interface or in the region of the dimer-dimer interface.

5. The chimeric streptavidin tetramer of claim 4, wherein the cysteine is situated at position H127.

6. The chimeric streptavidin tetramer of claim 1, wherein the streptavidin tetramer has an overall reduced binding affinity for biotin or a compound comprising biotin wherein a subunit modification consists of either a substitution of a hydrophobic amino acid for one or more amino acids present in the biotin binding domain or a deletion of one or more amino acids in the biotin binding domain.

7. The chimeric streptavidin tetramer of claim 1, wherein the streptavidin tetramer has a capacity to bind to a molecule other than streptavidin, biotin, or a compound comprising biotin, wherein a subunit modification consists of the substitution of cysteine for asparagine at amino acid position 94 and covalent attachment of the molecule to the cysteine.

8. The chimeric streptavidin tetramer of claim 1, wherein the streptavidin tetramer has an altered subunit affinity conferring an enhanced sensitivity to hydrostatic pressure wherein a subunit modification consists of the substitution of an amino acid selected from the group consisting of a positively-charged amino acid, a negatively charged amino acid, or a cysteine for an amino acid present either in the region of a monomer-monomer interface or in the region of the dimer-dimer interface.

9. A streptavidin tetramer having an altered subunit affinity conferring an enhanced sensitivity to hydrostatic pressure wherein a subunit modification consists of the substitution of an amino acid selected from the group consisting of a positively-charged amino acids a negatively charged amino acid, or a cysteine for an amino acid present either in the region of a monomer-monomer interface or in the region of the dimer-dimer interface.

10. The chimeric streptavidin tetramer of claim 9, wherein the subunit modification consists of the substitution of a cysteine for an amino acid present either in the region of a monomer-monomer interface or in the region of the dimer-dimer interface.

11. The chimeric streptavidin tetramer of claim 10, wherein the cysteine is situated at position H127.

12. A chimeric streptavidin tetramer comprising between one and three modified monomers,
   wherein the chimeric tetramer has one or more of the following characteristics:
   (i) an overall altered binding affinity for biotin or a compound comprising biotin wherein a subunit modification consists of either a substitution of a hydrophobic amino acid for one or more amino acids present in the biotin binding domain or a deletion of one or more amino acids in the biotin binding domain,
   (ii) an altered subunit affinity conferring an enhanced sensitivity to hydrostatic pressure wherein a subunit modification consists of the substitution of an amino acid selected from the group consisting of a positively-charged amino acid, a negatively charged amino acid, or a cysteine for an amino acid present either in the region of a monomer-monomer interface or in the region of the dimer-dimer interface, and
   (iii) a molecular label permitting monitoring of subunit association into tetramers having specific stoichiometric ratios of modified and unmodified subunits wherein a subunit modification consists of the substitution of cysteine for asparagine at amino acid position 94 and covalent attachment of the label to the cysteine, and,
   (iv) a capacity to bind to a molecule other than streptavidin, biotin, or a compound comprising biotin, wherein a subunit modification consists of the substitution of cysteine for asparagine at amino acid position 94 and covalent attachment of the molecule to the cysteine.

13. The chimeric tetramer of claim 12 wherein the chimeric tetramer has one or more of the following characteristics:
   (i) an overall altered binding affinity for biotin or a compound comprising biotin wherein a subunit modification consists of either a substitution of a hydrophobic amino acid for one or more amino acids present in the biotin binding domain or a deletion of one or more amino acids in the biotin binding domain, and
   (ii) an altered subunit affinity conferring an enhanced sensitivity to hydrostatic pressure wherein a subunit modification consists of the substitution of an amino acid selected from the group consisting of a positively-charged amino acid, a negatively charged amino acid, or a cysteine for an amino acid present either in the region of a monomer-monomer interface or in the region of the dimer-dimer interface.

14. An isolated collection of chimeric streptavidin tetramers wherein the tetramers are formed by mixing wildtype monomers and a single type of modified monomer,
   wherein the chimeric tetramer has one or more of the following characteristics:
      (i) an overall altered binding affinity for biotin or a compound comprising biotin wherein a subunit modification consists of either a substitution of a hydrophobic amino acid for one or more amino acids present in the biotin binding domain or a deletion of one or more amino acids in the biotin binding domain,
      (ii) an altered subunit affinity conferring an enhanced sensitivity to hydrostatic pressure wherein a subunit modification consists of the substitution of an amino acid selected from the group consisting of a positively-charged amino acid, a negatively charged amino acid or a cysteine for an amino acid present either in the region of a monomer-monomer interface or in the region of the dimer-dimer interface, and
      (iii) a molecular label permitting monitoring of subunit association into tetramers having specific stoichiometric ratios of modified and unmodified subunits wherein a subunit modification consists of the substitution of cysteine for asparagine at amino acid position 94 and covalent attachment of the label to the cysteine, and,
      (iv) a capacity to bind to a molecule other than streptavidin, biotin, or a compound comprising biotin, wherein a subunit modification consists of the substitution of cysteine for asparagine at amino acid position 94 and covalent attachment of the molecule to the cysteine.

15. An isolated chimeric streptavidin tetramer comprising between one and three modified monomers,
   wherein the tetramer is formed by mixing wildtype monomers and one, two, or three types of modified monomer,
   wherein the chimeric tetramer has one or more of the following characteristics:
      (i) an overall altered binding affinity for biotin or a compound comprising biotin wherein a subunit modification consists of either a substitution of a hydrophobic amino acid for one or more amino acids present in the biotin binding domain or a deletion of one or more amino acids in the biotin binding domain,
      (ii) an altered subunit affinity conferring an enhanced sensitivity to hydrostatic pressure wherein a subunit modification consists of the substitution of an amino acid selected from the group consisting of a positively-charged amino acid, a negatively charged amino acid, or a cysteine for an amino acid present either in the region of a monomer-monomer interface or in the region of the dimer-dimer interface, and
      (iii) a molecular label permitting monitoring of subunit association into tetramers having specific stoichiometric ratios of modified and unmodified subunits wherein a subunit modification consists of the substitution of cysteine for asparagine at amino acid position 94 and covalent attachment of the label to the cysteine, and,
      (iv) a capacity to bind to a molecule other than streptavidin, biotin, or a compound comprising biotin, wherein a subunit modification consists of the substitution of cysteine for asparagine at amino acid position 94 and covalent attachment of the molecule to the cysteine.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: protein (xi) SEQUENCE DESCRIPTION: SEQ ID NO:1:

TTTCGCAGCA ACGGTCCAAC CCAGAGCGGT TCCAGAA                                37

(2) INFORMATION FOR SEQ ID NO:2:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: protein (xi) SEQUENCE DESCRIPTION: SEQ ID NO:2:

TTTGAAAGCA ACGGTCCAAC CCAGAGCGGT TCCAGA                                 36

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: protein (xi) SEQUENCE DESCRIPTION: SEQ ID NO:3:

ACCGCGTCTG GTCAGTACGT TGGTGGTGCT GAA                                    33

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: protein (xi) SEQUENCE DESCRIPTION: SEQ ID NO:4:

CCTTCTCTGG TCAGTACGTT GGTGGTGCTG                                        30

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: protein (xi) SEQUENCE DESCRIPTION: SEQ ID NO:5:

GGTCGTACCG GAGGTCAGCA GCGACTGG                                          28

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: protein (xi) SEQUENCE DESCRIPTION: SEQ ID NO:6:

GGTCGTACCG GAGGTCAGCA GGACCTGG                                          28

(2) INFORMATION FOR SEQ ID NO:7:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: protein (xi) SEQUENCE DESCRIPTION: SEQ ID NO:7:

AGTTCTTGTT GACCTCCGGC ACCACCGAAG CTAACGCTTG G                   41

(2) INFORMATION FOR SEQ ID NO:8:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: protein (xi) SEQUENCE DESCRIPTION: SEQ ID NO:8:

CGCGGCTAAA TCCACCCTGG TTGGTCACGA CACCTTCACC AAAGTTAA              48

(2) INFORMATION FOR SEQ ID NO:9:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: protein (xi) SEQUENCE DESCRIPTION: SEQ ID NO:9:

CGCGTTTAAA TCCACCCTGG TTGGTCACGA CACCTTCACC AAAGTTAA              48

(2) INFORMATION FOR SEQ ID NO:10:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: protein (xi) SEQUENCE DESCRIPTION: SEQ ID NO:10:

AGCTTTTATT AGGAAGCTGC AGACGGTTTA ACTTTGGTGA AGGTGTCGTG ACCAACCAGG      60

GTGGATTTAG C                                                             71

(2) INFORMATION FOR SEQ ID NO:11:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: protein (xi) SEQUENCE DESCRIPTION: SEQ ID NO:11:

-continued

```
AGCTTTTATT AGGAAGCTGC AGACGGTTTA ACTTTGGTGA AGGTGTCGTG ACCAACCAGG        60

GTGGATTTAA A                                                            71
```